United States Patent
Mide et al.

(10) Patent No.: US 11,779,746 B2
(45) Date of Patent: Oct. 10, 2023

(54) FLUID TRANSFER CONNECTORS

(71) Applicant: CONCEPTOMED AS, Ballstad (NO)

(72) Inventors: Christian Mide, Ballstad (NO); Jimmy Gidö Schön, Ballstad (NO); Einar Bollvåg, Bodø (NO)

(73) Assignee: CONCEPTOMED AS, Ballstad (NO)

( * ) Notice: Subject to any disclaimer, the term of this patent is extended or adjusted under 35 U.S.C. 154(b) by 754 days.

(21) Appl. No.: 16/629,911

(22) PCT Filed: Jul. 9, 2018

(86) PCT No.: PCT/EP2018/068564
§ 371 (c)(1),
(2) Date: Jan. 9, 2020

(87) PCT Pub. No.: WO2019/011870
PCT Pub. Date: Jan. 17, 2019

(65) Prior Publication Data
US 2021/0138220 A1 May 13, 2021

(30) Foreign Application Priority Data
Jul. 10, 2017 (GB) .................................. 1711101

(51) Int. Cl.
*A61M 39/12* (2006.01)
*A61M 39/10* (2006.01)
*A61M 39/28* (2006.01)

(52) U.S. Cl.
CPC ........ *A61M 39/1011* (2013.01); *A61M 39/12* (2013.01); *A61M 39/284* (2013.01)

(58) Field of Classification Search
CPC .... A61M 39/284; A61M 39/12; A61M 39/28; A61M 39/287; A61M 39/288; A61M 39/1011; A61M 39/10; A61M 2039/1027
See application file for complete search history.

(56) References Cited

U.S. PATENT DOCUMENTS 4,473,369 A * 9/1984 Lueders .............. A61M 39/287
604/905
4,611,785 A * 9/1986 Steer ................... A61M 39/288
251/4

(Continued)

FOREIGN PATENT DOCUMENTS

DE 202012007845 U1 11/2013
EP 2705873 A1 3/2014

(Continued)

OTHER PUBLICATIONS

Notification of Transmittal of the International Search Report and Written Opinion (Form PCT/ISA/220), International Search Report (Form PCT/ISA/210), and Written Opinion of the International Searching Authority (Form PCT/ISA/237) for International Application No. PCT/EP2018/068564, dated Dec. 13, 2018, 15 pages.

(Continued)

*Primary Examiner* — David Bochna
(74) *Attorney, Agent, or Firm* — Withrow & Terranova, P.L.L.C.; Vincent K. Gustafson

(57) ABSTRACT

A fluid transfer connector comprises a medical standard connector part comprising a fluid transfer port, a connector part for flexible tubing, the connector part arranged to form a fluid connection with the fluid transfer port such that, in use, a fluid flow can pass between flexible tubing connected to the connector part and the fluid transfer port. The connector further comprises a moveable member arranged to interrupt the fluid flow in the flexible tubing when moved from a first position to a second position. The moveable member is further arranged to release a connection, in use, between the medical standard connector part and a corresponding adaptor part such as a female hub).

16 Claims, 16 Drawing Sheets

(56) References Cited

U.S. PATENT DOCUMENTS

| | | | | |
|---|---|---|---|---|
| 4,807,622 | A * | 2/1989 | Ohkaka | A61M 39/284 606/167 |
| 5,127,905 | A | 7/1992 | Lemieux | |
| 5,201,716 | A * | 4/1993 | Richard | A61B 5/150732 604/243 |
| 5,817,116 | A * | 10/1998 | Takahashi | F16L 55/10 606/167 |
| 5,951,519 | A * | 9/1999 | Utterberg | A61M 39/20 604/167.01 |
| 7,306,586 | B2 * | 12/2007 | Beaufore | A61M 25/0017 604/533 |
| 8,328,763 | B2 * | 12/2012 | Traversaz | A61M 5/14244 604/250 |
| 2004/0039373 | A1 * | 2/2004 | Harding | A61M 25/0014 604/533 |
| 2005/0107770 | A1 | 5/2005 | Schweikert et al. | |
| 2005/0253390 | A1 | 11/2005 | Blazek | |
| 2008/0208159 | A1 * | 8/2008 | Stanus | A61J 1/1475 604/408 |
| 2009/0270842 | A1 * | 10/2009 | Blocher | A61M 39/12 604/533 |
| 2010/0036322 | A1 * | 2/2010 | Rotem | A61M 5/14228 604/151 |
| 2010/0191193 | A1 * | 7/2010 | Pajunk | A61M 25/0014 604/250 |
| 2011/0006520 | A1 * | 1/2011 | Hall | A61M 39/00 285/383 |
| 2011/0077621 | A1 * | 3/2011 | Graham | A61M 25/01 604/528 |
| 2012/0004624 | A1 * | 1/2012 | Brown | A61M 39/287 604/250 |
| 2012/0083737 | A1 * | 4/2012 | Beck | A61M 5/14232 604/151 |
| 2013/0324975 | A1 * | 12/2013 | Douglas | A61M 39/283 604/328 |
| 2014/0074046 | A1 | 3/2014 | Dulong et al. | |
| 2016/0279032 | A1 | 9/2016 | Davis et al. | |
| 2017/0014616 | A1 | 1/2017 | Davis et al. | |
| 2018/0200499 | A1 * | 7/2018 | Mide | A61M 5/344 |

FOREIGN PATENT DOCUMENTS

| | | |
|---|---|---|
| EP | 3159024 A1 | 4/2017 |
| EP | 3162393 A1 | 5/2017 |
| WO | 9522369 A1 | 8/1995 |
| WO | 9848872 A1 | 11/1998 |
| WO | 2013164358 A1 | 11/2013 |
| WO | 2014020090 A1 | 2/2014 |
| WO | 2015014914 A1 | 2/2015 |
| WO | 2016162571 A1 | 10/2016 |

OTHER PUBLICATIONS

Search Report under Section 17(5) for United Kingdom Patent Application No. GB1711101.4 dated Jan. 31, 2018, 5 pages.

* cited by examiner

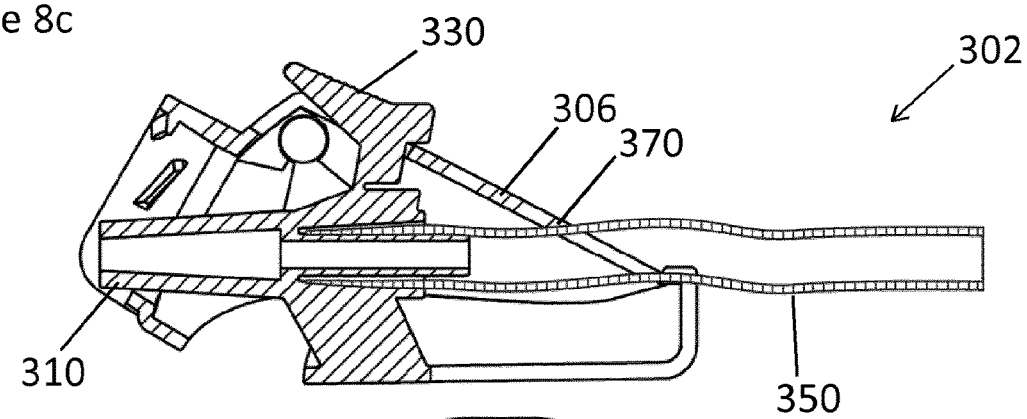
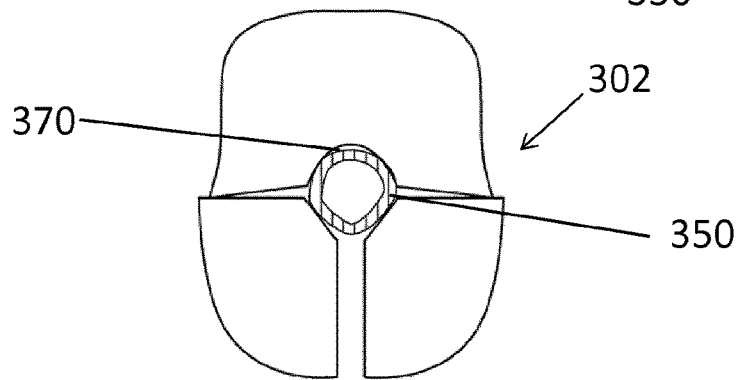
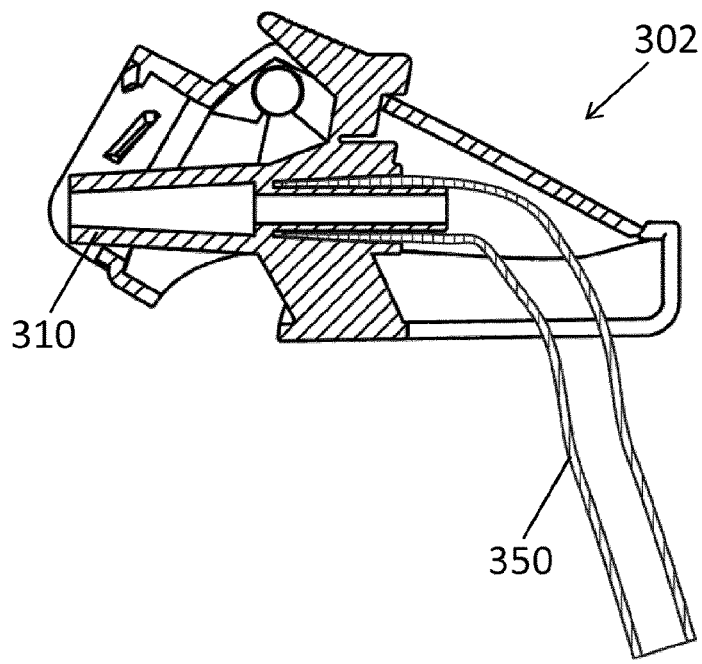
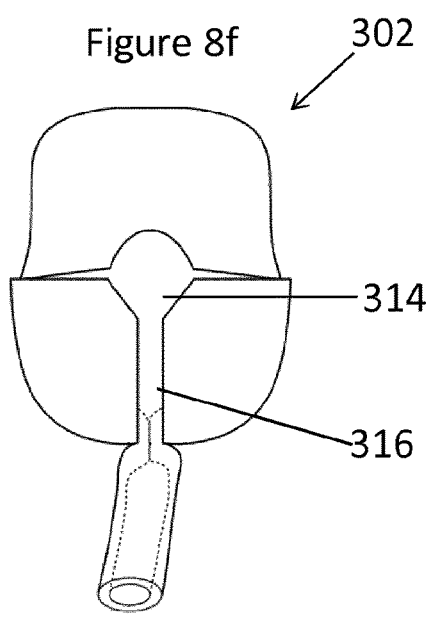

FLUID TRANSFER CONNECTORS

CROSS-REFERENCE TO RELATED APPLICATIONS

This application is a 35 U.S.C. § 371 national phase filing of International Application No. PCT/EP2018/068564 filed on Jul. 9, 2018 and further claims priority to United Kingdom Patent Application No. 1711101.4 filed on Jul. 10, 2017, wherein the disclosures of the foregoing applications are hereby incorporated by reference herein in their respective entireties.

TECHNICAL FIELD

The present invention relates to fluid transfer connectors and related fluid transfer systems.

BACKGROUND

The Applicant has previously devised solutions for easily disconnecting a contaminated needle from a syringe (or other fluid transfer device) using one hand as disclosed in WO 2013/164358, WO 2014/020090, WO 2015/014914 and WO 2016/162571. The Applicant's system uses a pivoting disconnecting member, e.g. lever member, to separate the needle hub from the syringe. By utilising a lever member the practitioner can, in a one handed operation, more easily disconnect the needle hub from the syringe and reduce the risk of needlestick injuries.

The Applicant has previously devised solutions compatible with standard Luer Slip and Luer Lock connectors. The Applicant has realised that its fluid transfer connections may find use in any situation where fluid is being transferred using devices or lines connected by Luer type connector parts. Luer connectors are standardised friction fittings using a 6% taper to make leak-free connections between a tapered male tip and its mating female part e.g. in medical equipment. In one example, a Luer type hub connected to a needle or other cannula may be used to infuse fluid substances i.e. intravenous (IV) therapy. A drip is one type of IV therapy. IV therapy may be used to correct electrolyte imbalances, to deliver medications or nutrition, for blood transfusion or as fluid replacement to correct dehydration. IV therapy can also be used for chemotherapy of cancer patients. A typical IV kit comprises flexible tubing that is used to convey fluid under gravity from a bag to the infusion site. The flexible tubing may carry male and/or female Luer Lock connectors at its ends to form a fluid-tight connection. A clamping device may be externally fitted to the flexible tubing.

When preparing an IV line, it is necessary to connect the flexible tubing to the bag and clamp the tubing while the line is filled with fluid. A needle or cannula is inserted into a patient's vein and usually carries a female Luer connector hub. It is a two-handed operation to connect a male Luer connector part to the hub as the parts must be screwed together. Typically the male Luer connector part is provided at one end of a flexible hose and a syringe is connected to a female Luer connector part at the other end of the hose for an initial fluid injection. To disconnect the syringe from the hose, the Luer connection is unscrewed and then the IV line can be connected to the hose instead. However, the twisting required to disconnect the syringe from the female Luer connector part can inadvertently loosen the Luer connection at the other end of the hose. It is problematic if the female Luer connector hub becomes exposed at the insertion site as it cannot easily be cleaned. The only way to deal with contamination is to remove the cannula from the patient and insert a new one, causing pain and unnecessary venous damage.

Once the IV line is connected to the female Luer connector part at the back end of the hose, the clamping device may be loosened so that fluid can flow down to the cannula. At various times it may be necessary to replace the IV line, which involves first clamping the line and then disconnecting the male Luer Lock connector at one end of the flexible tubing. Multiple steps are involved. If a user forgets to manually clamp the line then fluid can escape. It is a two-handed operation to disconnect the male Luer connector part from the female Luer connector hub carried by the hose. The conventional disconnection and connection of Luer lock connector parts brings a person's hands into close contact with the connector parts and carries a risk of contamination.

The present invention aims to address or at least mitigate one or more of the problems outlined above.

BRIEF SUMMARY OF INVENTION

When viewed from a first aspect, the present invention provides a fluid transfer connector, the connector comprising:

a Luer connector part comprising a fluid transfer port having a tapered surface to form a friction fitting with a corresponding Luer part;

a connector part for flexible tubing that forms a fluid connection with the fluid transfer port such that, in use, a fluid flow can pass between flexible tubing connected to the connector part and the fluid transfer port; and a moveable member arranged to interrupt the fluid flow in the flexible tubing when moved from a first position to a second position.

It will be appreciated that such a connector provides an alternative to a conventional Luer Lock connector and separate clamping device, for example a roller clamp, slide clamp or tubing clip. Typically a user must manually apply such clamping devices to an IV line before separately connecting or disconnecting a Luer Lock connector. According to embodiments of the present invention, a moveable member integrated with the fluid transfer connector can be used to control or shut off flow through the flexible tubing. Such connectors conveniently provide a dual function.

In some embodiments, a user may manually connect flexible tubing to the connector part before use. A press fit or additional Luer connection may be used.

In some embodiments, flexible tubing may be permanently connected to the connector part and form part of the fluid transfer connector. For example, flexible tubing may be welded or glued onto the connector part.

In one or more embodiments, the flexible tubing may run externally of the connector. Similar to conventional IV tubing and extension lines, the flexible tubing may comprise a Luer connector part at its other end. In some other embodiments, the flexible tubing may be connected to the connector part internally of the connector. The flexible tubing is acted upon by the moveable member to control or stop the fluid flow to the fluid transfer port. In these embodiments, the flexible tubing may be connected to another fluid transfer tube that runs externally of the connector, this fluid transfer tube being flexible or rigid.

As mentioned above, the connector may comprise a pre-connected flexible tubing or flexible tubing connected to the connector part in use.

In some preferred embodiments, the moveable member is arranged to interrupt the fluid flow in the flexible tubing by moving to at least partially deform the flexible tubing. The moveable member may work in a similar way to known IV line clamps, thereby making it familiar to users. In one or more embodiments the connector further comprises a clamping surface, wherein the moveable member is arranged to interrupt the fluid flow in the flexible tubing by moving to press the flexible tubing onto or against the clamping surface. In one or more embodiments the connector further comprises a clamping channel, wherein the moveable member is arranged to interrupt the fluid flow in the flexible tubing by moving to push the flexible tubing into the clamping channel. The moveable member may comprise one or more clamping members, such as protrusions, arranged to bring the flexible tubing into contact with the clamping surface or channel as the moveable member moves from the first position to the second position.

In some embodiments, the main function of the moveable member may be to interrupt the fluid flow to the fluid transfer port, i.e. an integrated metering or clamping function. Disconnection of a corresponding Luer part from the Luer connector part comprising the fluid transfer port may take place independently, for example manual disconnection as is conventional. However, the Applicant has realised that it may be particularly advantageous for the moveable member to also act to disconnect a corresponding Luer part from the Luer connector part. This may facilitate single-handed disconnection rather than two-handed unscrewing. Thus, in or more preferred embodiments, the moveable member is further arranged to release the friction fitting with a corresponding Luer part.

In some embodiments the moveable member may be arranged to release the friction fitting while moving from the first position to the second position. In other words, disconnection of a Luer part from the Luer connector part may take place at the same time as interrupting the fluid flow to the fluid transfer port. This may be possible where the fluid flow is not pressurised, for example gravity flow through an IV line. However, it is often preferable for the fluid flow to be reduced, and preferably shut off, before the connector is released. Thus in some embodiments the moveable member is further arranged to release the friction fitting with a corresponding Luer part when moved from the second position to a third position. This means that the fluid flow is interrupted in a first stage before any disconnection of the Luer part takes place.

In various embodiments, the moveable member is arranged to release the friction fitting by moving along the tapered surface of the fluid transfer port to push away the corresponding Luer part. Some examples of such a disconnecting member are seen in WO 2013/164358, the contents of which are hereby incorporated by reference. In some such embodiments, the fluid transfer connector further comprises a Luer adaptor as the corresponding Luer part connected to the Luer connector part and the moveable member is arranged to move along the tapered surface to push off the Luer adaptor and thereby release the friction fitting. The Luer adaptor may comprise any standard Luer type adaptor, e.g. a Luer Lock or Luer Slip adaptor. Such a mechanism may be sufficient for a Luer Slip connector part. As will be described further below, in embodiments where the connector comprises a Luer Lock connector part, the moveable member may move a latch or screw thread out of engagement with the corresponding Luer part or adaptor before releasing the friction fitting. This is described in detail in WO 2015/014914.

The Applicant has therefore devised a fluid transfer connector that combines Luer disconnection with control or blocking of the fluid flow through the connector. This is considered novel and inventive in its own right. Thus when viewed from a second aspect, the present invention provides a fluid transfer connector comprising:

a Luer connector part comprising a fluid transfer port having a tapered surface to form a friction fitting with a corresponding Luer part;

a fluid transfer channel in fluid communication with the fluid transfer port;

a moveable member arranged to:

interrupt the fluid communication between the fluid transfer channel and the fluid transfer port when moved from a first position to a second position; and release the friction fitting with a corresponding Luer part when moved from the first position to the second position and/or from the second position to a third position.

Such a fluid transfer connector does not rely on flexible tubing to enable interruption of the fluid communication within the connector. Any suitable kind of valve mechanism may be integrated with the connector and the moveable member arranged to operate the valve mechanism as well as acting to release the friction fitting.

Although the friction fitting may be at least partially released at the same time as the fluid communication is interrupted, it is preferable to release the friction fitting with a corresponding Luer part at a later stage, preferably when the moveable member is moved from the second position to a third position. The fluid communication may be shut off when the moveable member reaches the second position.

In at least some embodiments, the moveable member is arranged to interrupt the fluid communication by moving a valve part to at least partially block the fluid communication with the fluid transfer port in the second position. Preferably the valve part completely blocks any fluid communication with the fluid transfer port in the second position. For example, the moveable member may move the valve part of a stopcock or other valve mechanism.

In various embodiments of either the first or second aspect of the invention, the Applicant has recognised that it can be desirable to lock the moveable member in the first position so that the moveable member is not inadvertently operated. This can be especially important when the fluid transfer connector is in situ in an IV line and a patient may be moving around, e.g. rolling over in bed, while the line is connected. Accordingly the connector may further comprise a locking member to hold the moveable member in the first position. Manual intervention is preferably required to unlock the moveable member before it can be moved out of the first position. The connector may comprise a button or other actuator that must be depressed to open the lock. This means there is an initial unlocking stage before the moveable member can be moved from the first position to the second position in a second stage. In an optional third stage, movement of the moveable member may act to release the friction fitting, as is described above. The second and third stages may overlap or they may be distinct.

In addition, or alternatively, the Applicant has recognised that it can be desirable to lock the moveable member in the second and/or third position so that the moveable member continues to interrupt (e.g. block) fluid flow or communication with the fluid transfer port. This ensures a reliable clamping function. Thus in some embodiments the connector may further comprise a latch to hold the moveable member in the second and/or third position. The latch may be arranged to overcome a resilient bias acting on the moveable member. For example, the connector may comprise a spring member applying a resilient bias. Alternatively, the moveable member may be deformed as it moves out of the first position and this may result in a natural resilient bias. The resilient bias may act to return the moveable member to the first position unless the latch is applied. The latch may be manually applied, but preferably the latch operates automatically when the moveable member reaches the second and/or third position. While the latch is applied, a user can disconnect the corresponding Luer part without any fluid flowing out through the fluid transfer port. The fluid transfer connector may be connected to another Luer part. Once the new connection is ready for use, the latch may be released. The connector may comprise a latch release separate to the moveable member. In at least some embodiments the moveable member is resiliently biased to return to the first position when the latch release is operated.

In one or more embodiments, the lock arranged to hold the moveable member in the first position may comprise a locking member in the form of a hinged strut supporting the moveable member. The hinged strut may be a plastic part comprising a living hinge. A user may need to press on the moveable member with a predetermined force before the strut will hinge to allow the moveable member to move from the first position to the second position. In one or more embodiments, the lock arranged to hold the moveable member in the first position may comprise an over-centre mechanism.

In one or more embodiments, the moveable member may be elastically deformable. In some embodiments this can be used to reduce the risk of accidental operation. In at least some embodiments, the connector may comprise engagement features operating between the moveable member and the connector which engage with one another to inhibit the moveable member from moving, the connector being arranged such that, upon application of a force to the moveable member, the moveable member deforms so that the engagement features are no longer in engagement with one another, thereby allowing the moveable member to move out of the first position. In such embodiments, the engagement features may comprise at least one protrusion and at least one complementary recess, for example one or more protrusions located on or in the connector and one or more complementary recesses located on the moveable member.

In one or more embodiments, the connector may comprise a lock arranged to hold the moveable member in one or more intermediate positions between the first position and the second and/or third position. For example, the lock may comprise a ratchet mechanism. This can facilitate a metering function of the fluid flow. Furthermore, it can assist with interrupting the fluid flow and then delaying before the moveable member is moved further e.g. to disconnect the friction fitting.

In various of the embodiments described above, the moveable member is arranged to release the friction fitting between the Luer connector part and a corresponding Luer part. This can make it possible for a user to disconnect the Luer parts in a single-handed operation rather than needing two hands to pull and/or twist the Luer parts. The moveable member may not always act to automatically interrupt the fluid flow through the connector. In some situations it may be preferable for disconnection to be entirely independent of any clamping function. However the Applicant has realised that the connector can conveniently enable manual clamping without needing a separate clamp, as is conventional. This is considered novel and inventive in its own right. Thus when viewed from a third aspect, the present invention provides a fluid transfer connector, the connector comprising:

a Luer connector part comprising a fluid transfer port having a tapered surface to form a friction fitting with a corresponding Luer part;

a connector part for flexible tubing that forms a fluid connection with the fluid transfer port such that, in use, a fluid flow can pass between flexible tubing connected to the connector part and the fluid transfer port;

a moveable member arranged to release the friction fitting with a corresponding Luer part when moved from a first position to a second position; and a clamping part arranged to receive the flexible tubing in a clamped position when the flexible tubing is manually engaged with the clamping part.

The clamping part is preferably integrated with the fluid transfer connector. At least the connector part and the clamping part may be monolithic, for example formed as a single plastic moulding. During use, the flexible tubing may be pushed or pulled into manual engagement with the clamping part. The manual engagement with the clamping part can be independent of movement of the moveable member. This means that clamping can be carried out entirely separately from release of the friction fitting. These two actions may take place at different points in time. The flexible tubing may be deformed in the clamped position so that there is no fluid flow between the flexible tubing and the fluid transfer port.

The clamping part may extend in a different direction to the Luer connector part. The clamping part may be diametrically opposed to the Luer connector part. This can help to provide a substantially straight-through flow. The clamping part may comprise a wall having a V-shaped slit. The wall may In various embodiments described above, fluid is prevented from leaving the connector through the fluid transfer port by internally interrupting the flow or manually engaging a clamping part. In addition, or alternatively, it may be desirable to block the fluid transfer port itself. This can be achieved, for example, by covering or sealing the end of fluid transfer port. In one or more embodiments, the moveable member is further arranged to block or cover the fluid transfer port when moved from the first position to the second position or to a further position (e.g. the third position mentioned above). This prevents outflow from the fluid transfer port and/or contamination when there is no connection in place. This can be especially important when the Luer connector part is left exposed for a period of time, for example while a new IV line is prepared.

This is considered novel and inventive in its own right. Thus when viewed from a another aspect, the present invention provides a fluid transfer connector comprising:

a Luer connector part comprising a fluid transfer port having a tapered surface to form a friction fitting with a corresponding Luer part; and a moveable member arranged to block or cover the fluid transfer port when moved from a first position to a second position.

The moveable member is preferably arranged to externally block or cover the fluid transfer port. This is unusual, as normally the fluid transfer port is left uncovered or covered with a separate cap when the connector is not in use. For example, the moveable member may comprise a collar extending at least partially around the Luer connector part. In addition, or alternatively, the moveable member or another part of the connector may comprise an absorbent pad arranged to catch drips from the fluid transfer port.

In some preferred embodiments will now be described that are applicable to any of the aspects of the invention.

The moveable member may comprise one or more of a slider, lever, arm, sleeve, or any other member that can be moveably mounted to the connector. In some preferred embodiments the moveable member comprises a lever member pivotally mounted to the fluid transfer connector. The connector may comprise one or more lever members.

In a set of embodiments the moveable member comprises a lever member pivotally mounted to the device. The lever member may comprise an actuation portion and be pivotally mounted such that the action of a user pressing on the actuation portion causes the lever member to pivot. The lever member may comprise a disconnection arm and be pivotally mounted such that the action of a user pressing on the actuation portion causes the disconnection arm to tilt relative to the Luer connector part and push along the tapered surface. A forward facing surface of the disconnection arm may therefore rotate at the same time as moving forwards along the tapered surface. The Applicant has realised that a lever member acts to amplify the force applied by a user to the actuation portion and this means that a user may only need to press relatively lightly even though a larger force is needed to release the friction fitting. This makes disconnection easier.

The lever member may be manually operated, starting from the first position. In some embodiments the lever member may be mounted to the connector without any resilient bias. The lever member may be manually pivoted back to the first position or moved back to the first position when another corresponding Luer part is fitted to the Luer connector part. In other embodiments it is preferable that the lever member is pivotally mounted to the connector with a resilient bias that tends to bias the lever member into the first position. A user must then overcome this resilient bias to pivot the lever member out of the first position. This helps to avoid the lever member being operated accidentally. A resiliently-biased lever member may provide for one-hand operation. Such arrangements are described in more detail in WO2013/164358, the contents of which are hereby incorporated by reference.

In some embodiments the connector may comprise a spring member, e.g. arranged against the lever member, to provide the resilient bias. In some other embodiments the lever member may be pivotally mounted to the connector so as to provide its own resilient bias. For example, the lever member may deform elastically, at least to a degree, when a user presses on the actuation portion so as to cause the disconnection arm to tilt and, when the user removes the pressing force, the lever member may return to its original form and hence move the disconnection arm back.

The moveable member, whether a lever member or otherwise, may comprise a Luer Lock engagement part. The Luer Lock engagement part may be a latch or threaded collar that positively engages with the outer threads of a corresponding Luer Lock part. The Luer Lock engagement part may comprise means for gripping a hub or adaptor in a locked position. This may include a snap-fit connection, latch means, gripping fingers, etc. that positively engage i.e. grip a hub when it is connected by the friction fitting. This may be particularly suitable for high pressure fluid connections e.g. when transferring or collecting more viscous fluids. In some embodiments the Luer Lock engagement part comprises a threaded collar, e.g. a semi-circular collar carrying an internal thread. Such a threaded collar may be brought into engagement with a corresponding Luer Lock part when the moveable member is in the first position. When the moveable member is moved from the first position to the second position, and/or from the second position to the third position, the threaded collar may be moved out of engagement with a corresponding Luer Lock part. In embodiments wherein the moveable member is arranged to release the friction fitting, the moveable member may move the threaded collar out of engagement with a corresponding Luer Lock part before a part of the moveable member is arranged to move along the tapered surface of the Luer connector part to release the friction fitting. Some such arrangements are described in more detail in WO 2015/014914, the contents of which are hereby incorporated by reference.

The Luer connector part may comprise a male Luer connector part or a female Luer connector part. For example, a male Luer connector part may comprise a tapered male tip and a female Luer connector part may comprise a tapered female socket.

The present invention extends to a fluid transfer system comprising a fluid transfer connector as described above, and one or more sections of flexible tubing connected to the fluid transfer connector. Each section of flexible tubing may be connected to the fluid transfer connector by a Luer part, for example a male or female Luer Lock connector part. In some embodiments, to ensure compatibility with existing systems, the Luer connector part is a male Luer connector part and the fluid transfer connector is pre-connected to a flexible tubing comprising a female Luer connector part at its distal end.

All references herein to a Luer connector part are intended to relate to a Luer lock or a Luer slip connector part, e.g. a connector part in accordance with the International Standard ISO 80369-7. The standard ISO 80369-7:2016 specifies dimensions and requirements for the design and functional performance of Luer connectors intended to be used for connections in intravascular applications or hypodermic connections in hypodermic applications of medical devices and accessories. These Luer connector parts have a standard 6% tapered surface to provide a so-called Luer Slip connection, and optionally include a threaded collar to provide a standard Luer Lock connection. Although standard Luer Slip or Luer Lock connections use a male tapered tip that fits inside a female hub or adaptor, it is envisaged that this could be reversed and the fluid transfer tip could be a female part having an internal taper to form friction fit with a corresponding male hub, as is mentioned above.

While the description above refers to fluid transfer connectors comprising a Luer connector part, the Applicant has recognised that the whole of this disclosure may be applied to any fluid transfer connector meeting at least one of the ISO 80369 series of small-bore connector standards for fluid connectors in healthcare applications. The aim of this series of standards is to prevent misconnections between fluid transfer lines for different clinical uses, e.g. between enteral feeding tubes and IV lines. ISO 80369-1:2010 specifies the healthcare fields in which fluid transfer connectors are intended to be used. These healthcare fields of use include, but are not limited to, applications for: breathing systems and driving gases; enteral and gastric; urethral and urinary; limb cuff inflation; neuraxial devices; intravascular or hypodermic.

Thus when viewed from a further aspect, the present invention provides a fluid transfer connector, the connector comprising:

a medical standard connector part comprising a fluid transfer port;

a connector part for flexible tubing, the connector part arranged to form a fluid connection with the fluid transfer port such that, in use, a fluid flow can pass between flexible tubing connected to the connector part and the fluid transfer port; and a moveable member arranged to interrupt the fluid flow in the flexible tubing when moved from a first position to a second position.

It will be understood that what is meant by a medical standard connector part is a connector part meeting the requirements of one of the ISO 80369 series of small-bore connector standards. Optionally, the connector part for flexible tubing may also be a medical standard connector part, i.e. a connector part meeting the requirements of one of the ISO 80369 series of small-bore connector standards.

In a set of embodiments, the medical standard connector part is a Luer connector part. A Luer connector part is compliant with ISO 80369-7 for connections in intravascular applications or hypodermic connections in hypodermic applications of medical devices and accessories.

In another set of embodiments, the medical standard connector part is an ENFit connector part. An ENFit connector part is compliant with ISO 80369-3 for connections on enteral medical devices and accessories. Compatible enteral medical devices include enteral feeding sets, enteral drainage sets, enteral syringes, and patient interface devices including access ports. For example, the ENFit connector part may comprise a male connector tip and a coaxial connection collar. The male connector tip may have a tapered lead-in portion. The coaxial connection collar may be internally threaded. Such ENFit connector parts are dimensioned to prevent misconnections with Luer connector parts. Some examples of such ENFit connector parts are disclosed in US 2016/0279032 and US 2017/0014616, the contents of which are hereby incorporated by reference.

In another set of embodiments, the medical standard connector part is an NRFit connector part. An NRFit connector part is compliant with ISO 80369-6 for connections in neuraxial applications. Neuraxial applications involve the use of medical devices intended to administer medications to neuraxial sites, wound infiltration anaesthesia delivery, and other regional anaesthesia procedures or to monitor or remove cerebro-spinal fluid for therapeutic or diagnostic purposes. For example, the NRFit connector part may comprise a male tapered tip surrounded by a coaxial collar that is internally threaded. Such NRFit connector parts are dimensioned to prevent misconnections with Luer connector parts.

It will be appreciated that any of the features of a fluid transfer connector part described herein, in the context of a Luer connector part, may equally be applied to ENFit or NRFit connector parts. In particular, any of the clamping features described herein apply equally to embodiments wherein the connector part has the fluid transfer port comprised in an ENFit or NRFit connector part instead of a Luer connector part.

In those embodiments comprising an ENFit or NRFit connector part, the moveable member may be further arranged to release a connection between the ENFit or NRFit connector part and a corresponding ENFit or NRFit adaptor part. More generally, in a preferred set of embodiments, the moveable member is further arranged to release a connection, in use, between the medical standard connector part and a corresponding adaptor part. The connection between the medical standard connector part and a corresponding adaptor part may comprise at least a friction fitting. In addition to the friction fitting, the connection between the medical standard connector part and a corresponding adaptor part may further comprise a positive engagement.

As is mentioned above, in embodiments wherein the corresponding adaptor part is a Luer Lock part, the moveable member may comprise a latch, threaded collar or other gripping means that positively engages with the outer threads of the corresponding Luer Lock part. Some such arrangements are described in more detail in WO 2015/014914, the contents of which are hereby incorporated by reference.

In embodiments wherein the corresponding adaptor part is an ENFit or NRFit adaptor part, the moveable member may comprise a threaded collar, e.g. a semi-circular collar carrying an internal thread. Thus, more generally, in various embodiments the moveable member may comprise a threaded collar. Such a threaded collar may be brought into engagement with a corresponding ENFit or NRFit adaptor part (or other medical standard adaptor part) when the moveable member is in the first position. When the moveable member is moved from the first position to the second position, and/or from the second position to the third position, the threaded collar may be moved out of engagement with a corresponding adaptor part. In embodiments wherein the moveable member is arranged to release a friction fitting, the moveable member may move the threaded collar out of engagement with a corresponding adaptor part before releasing the friction fitting.

In some preferred embodiments, the moveable member is arranged to push against the adaptor part and thereby release the connection. For example, the moveable member is arranged to release the connection by moving along a surface of the medical standard connector part to push away the corresponding adaptor part. As mentioned above, the connection may comprise a friction fitting. In some preferred embodiments, the moveable member is arranged to move along a tapered tip of the medical standard connector part to push away the corresponding adaptor part.

In any one or more of the embodiments described above, preferably the moveable member is arranged to release the connection when moved from the second position to a third position, i.e. to a different position. This means that the fluid flow is interrupted in a first stage before any disconnection of the adaptor part takes place. In various embodiments, the moveable member may be moved directly from the second position to the third position. The second and third positions may be subsequent positions within a continuous range of movement of the moveable member. This means that a single operation of the moveable member may act to first interrupt the fluid flow and subsequently release the connection.

There is further disclosed herein a fluid transfer connector or connection comprising an adaptor part connected to the medical standard connector part. Preferably, the moveable member is arranged to release the connection by pushing against the adaptor part. In various embodiments, the moveable member is arranged to move along a tapered tip of the medical standard connector part to push away the adaptor part. It will be appreciated that the adaptor part may also meet the requirements of one of the ISO 80369 series of small-bore connector standards.

In any one or more of the embodiments described above, the fluid transfer connector may comprise a fluid transfer channel in fluid communication with the fluid transfer port. In such embodiments, the moveable member is preferably arranged to: interrupt the fluid communication between the fluid transfer channel and the fluid transfer port when moved from a first position to a second position; and release a connection, in use, between the medical standard connector part and a corresponding adaptor part when moved from the first position to the second position and/or from the second position to a third position.

Thus when viewed from a further aspect, the present invention provides a fluid transfer connector, the connector comprising:

a medical standard connector part comprising a fluid transfer port;

a fluid transfer channel in fluid communication with the fluid transfer port; and a moveable member arranged to: interrupt the fluid communication between the fluid transfer channel and the fluid transfer port when moved from a first position to a second position; and release a connection, in use, between the medical standard connector part and a corresponding adaptor part when moved from the first position to the second position and/or from the second position to a third position.

Such a fluid transfer connector combines disconnection with control or blocking of the fluid flow through the connector. For example, any suitable kind of valve mechanism may be integrated with the connector and the moveable member arranged to operate the valve mechanism as well as acting to release the connection. Although the connection may be at least partially released at the same time as the fluid communication is interrupted, it is preferable to release the connection with a corresponding adaptor part at a later stage, preferably when the moveable member is moved from the second position to a third position.

The fluid communication may be shut off when the moveable member reaches the second position.

When viewed from a yet further aspect, the present invention provides a fluid transfer connector, the connector comprising:

a medical standard connector part comprising a fluid transfer port;

a connector part for flexible tubing that forms a fluid connection with the fluid transfer port such that, in use, a fluid flow can pass between flexible tubing connected to the connector part and the fluid transfer port;

a moveable member arranged to release a connection, in use, between the medical standard connector part and a corresponding adaptor part when moved from a first position to a second position; and a clamping part arranged to receive the flexible tubing in a clamped position when the flexible tubing is manually engaged with the clamping part.

When viewed from a yet further aspect, the present invention provides a fluid transfer connector comprising:

a medical standard connector part comprising a fluid transfer port; and a moveable member arranged to block or cover the fluid transfer port when moved from a first position to a second position.

Embodiments of these further aspects of the invention may replace a Luer connector part with a medical standard connector part, but are otherwise described in detail above.

BRIEF DESCRIPTION OF DRAWINGS

Some preferred embodiments of the present invention will now be described, by way of example only, and with reference to the accompanying drawings, in which:

FIGS. 8a-f show operational steps for the fluid transfer connector seen in FIG. 6 and FIG. 7;

DETAILED DESCRIPTION OF PREFERRED EMBODIMENTS OF THE INVENTION

Figure 1:
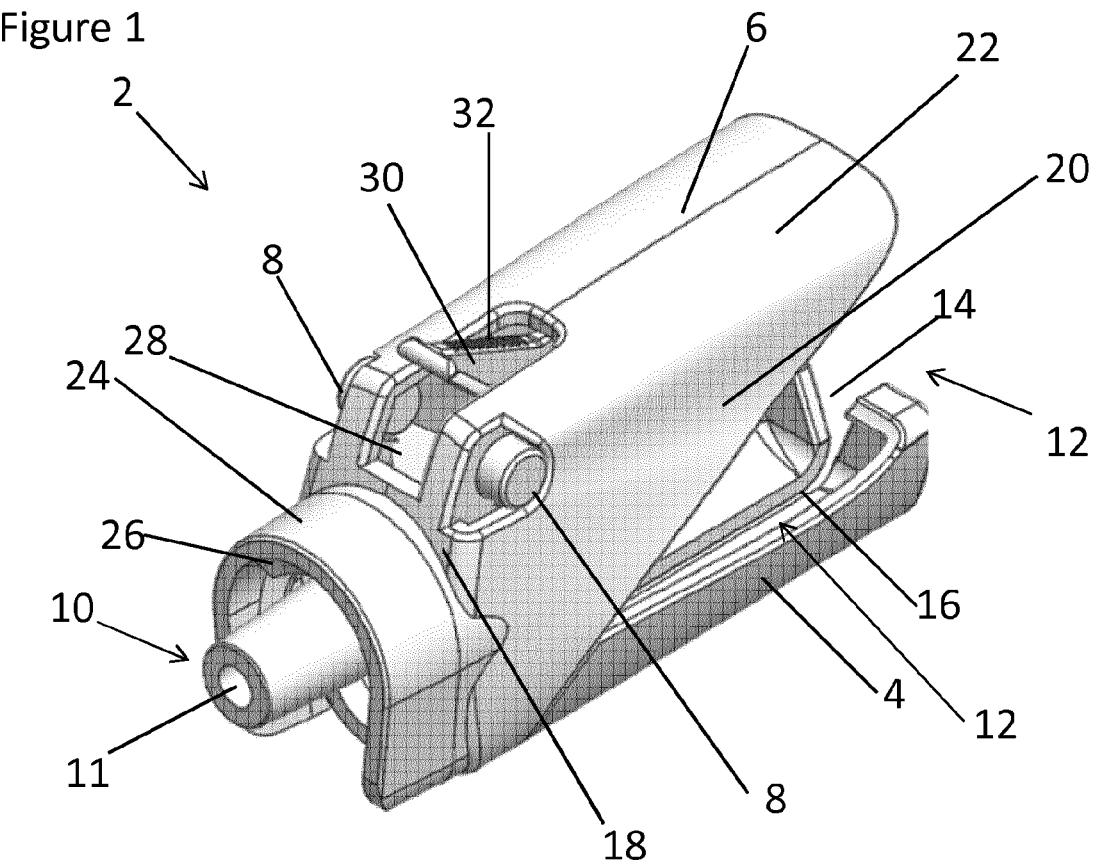
FIG. 1 shows a perspective view of a first embodiment of a fluid transfer connector.

FIG. 1 shows a forward perspective view of a fluid transfer connector 2 in accordance with an embodiment of the present invention. The fluid transfer connector 2 comprises a base portion 4 and a moveable member i.e. a pivotally mounted moving member in the form of a lever member 6. The lever member 6 is pivotally mounted to the base portion 4 by axle points 8. The base portion 4 and lever member 6 together form a hollow structure, as can be seen more clearly in FIG. 2. The base portion 4 comprises a Luer connector part in the form of a tapered male connector tip 10, at its forward end, which defines a fluid transfer port 11 there through. The fluid transfer port 11, as a result of being defined by the tapered male connector tip 10, has a tapered surface and it is the outer tapered surface that forms a friction fitting with a corresponding Luer part or adaptor (not shown). Connection and disconnection of a Luer part/adaptor to the tapered male connector tip 10 is described below with reference to FIGS. 3a-3f. The base portion 4 further comprises a hose clamp 12 comprising a V-shaped opening 14 located at the rear of the base portion 4. The V-shaped opening extends into an elongate slot 16 which runs along the base portion 4. The elongate slot 16 extends from the base of the V-shaped opening 14 and has a narrower extent than the mouth of the V-shaped opening 14.

The pivotally mounted lever member 6 comprises a front surface 18 which extends around the tapered male connector tip 10 and further comprises side surfaces 20 which extend away from the front surface 18 towards the rear of the fluid transfer connector 2. The side surfaces 20 also comprise an actuation surface 22 arranged on top of the lever member 6. It is the actuation surface 22 on which a user can press upon to pivot the lever member 6. Extending from the front surface 18 of the lever member 6 is a hemi-circular collar 24 which comprises an internal thread 26. The internal thread 26 may cooperate with a corresponding Luer part, comprising an externally threaded hub, which may be connected to the tapered male connector tip 10. An aperture 28 extends from the actuation surface 22 onto the front surface 18 and receives a locking member 30 which extends from the base portion 4. The locking member 30 comprises a ridged section 32 designed to provide additional grip for a user. The locking member 30 will be described in more detail in relation to FIGS. 9a-d.

Figure 2:
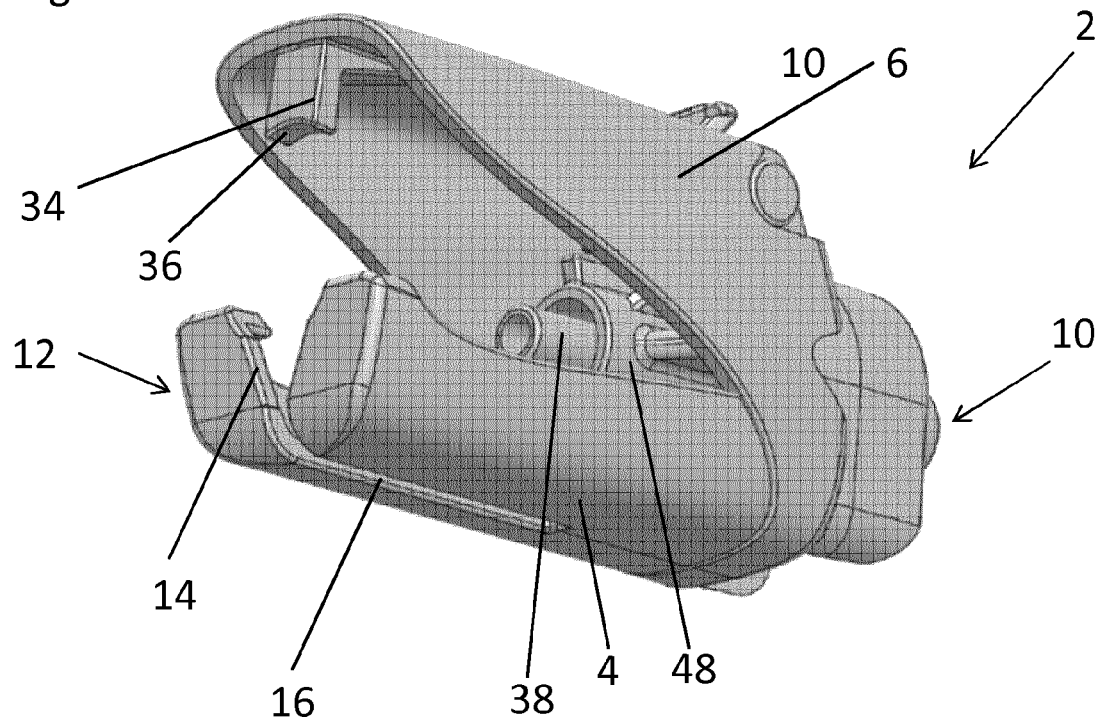
FIG. 2 shows a rear perspective view of the fluid transfer connector seen in FIG. 1.

FIG. 2 shows a rear perspective view of the fluid transfer connector 2. The lever member 6 comprises a downwardly projecting clamping member 34 arranged at the rear of the lever member 6 and aligned such that when the lever member 6 is pivoted it moves towards the V-shaped opening 14. The clamping member 34 has a rounded contact edge 36 arranged to come into contact with a hose (not shown) within the fluid transfer connector 2. The purpose of the rounded edge 36 is to provide for better contact with a hose and also reduce the risk of damage to the hose.

The fluid transfer connector 2 further comprises an internal connector part comprising a male connector tip 38 arranged to receive a hose, flexible tubing or other fluid transfer component. The internal male connector tip 38 is part of the base portion 4 and is partially surrounded by structure 48. FIG. 2 also shows how the elongate slot 16 extends along part of the length of the base portion 4.

Figure 3A:
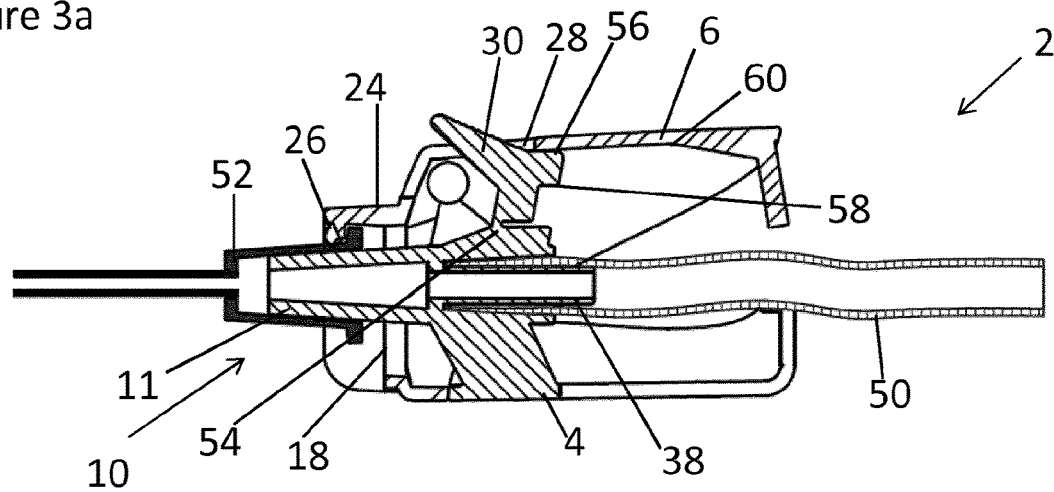
FIGS. 3a-f show the operational steps for the fluid transfer connector seen in FIG. 1 and FIG. 2.
Figure 3B:
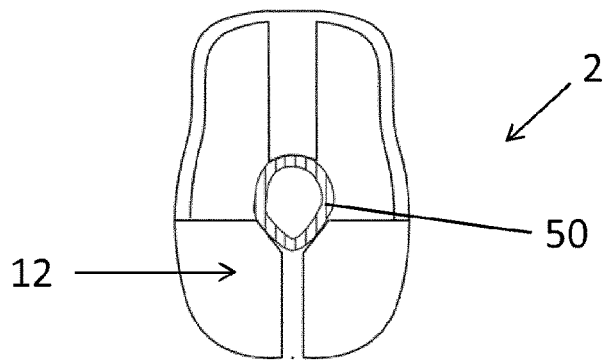
Figure 3C:
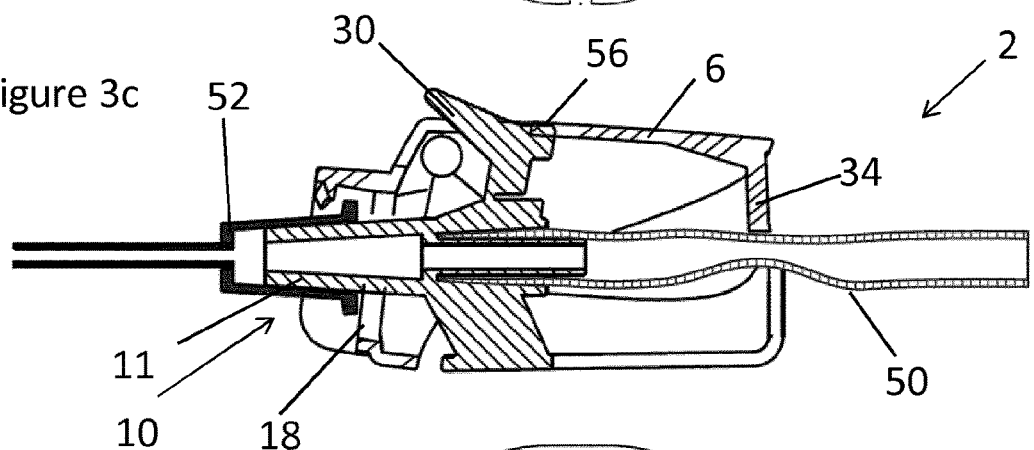
Figure 3D:
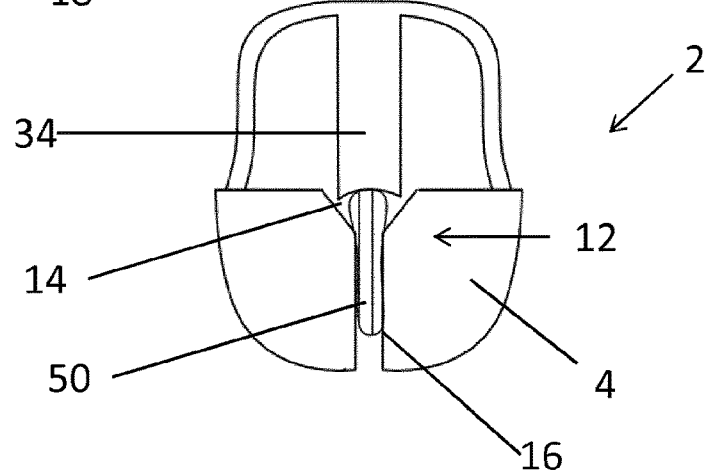
Figure 3E:
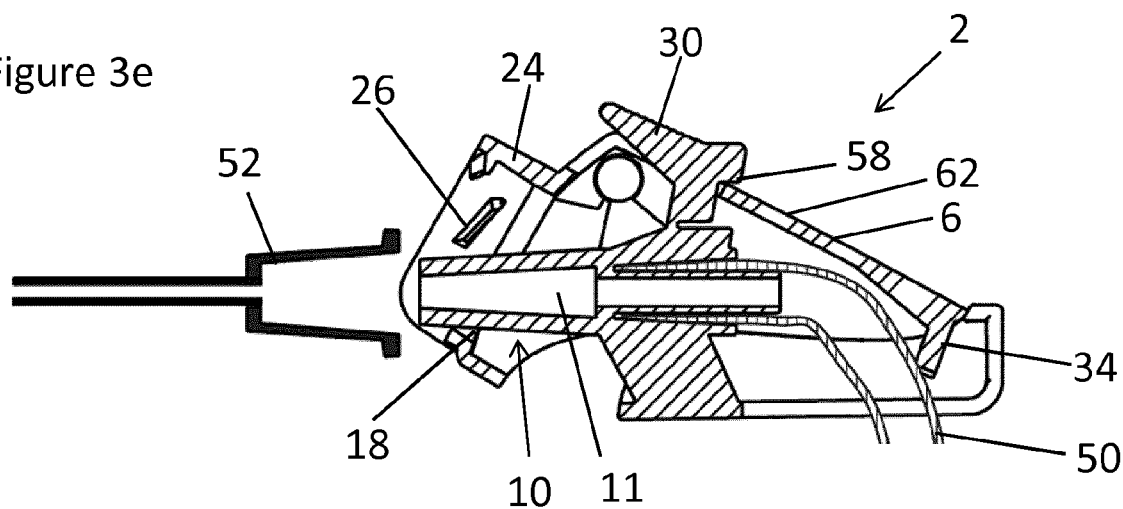

FIGS. 3a-f show the fluid transfer connector 2 as seen in FIGS. 1 and 2, attached to a flexible tubing e.g. hose 50 and a corresponding Luer or adaptor part e.g. female hub 52. The hose 50 is connected to the male connector part 38, e.g. by an interference fit or a permanent attachment, e.g. welded or crimped on. It can be seen that there is a fluid connection through the connector 2 between the connector part 38 and the fluid transfer port 11 such that, in use, a fluid flow can pass between the hose 50 and the port 11. These figures show how the fluid transfer connector 2 can be used to clamp the hose 50 and release the female hub 52. FIGS. 3a, 3c and 3e each show a cross sectional view of the fluid transfer connector 2 during different stages of the clamping and disconnection process, and FIGS. 3b, 3d and 3f each show corresponding views of the rear of the fluid transfer connector 2.

FIG. 3a shows the fluid transfer connector 2 attached to a flexible tubing hose 50. The hose 50 is attached to the male connector tip 38 of the internal connector part. The hose 50 extends away from the internal male connector tip 38 and passes out of the rear of the fluid transfer connector 2. Connected to the tapered male connector tip 10 of the Luer connector part is a corresponding Luer part, a female Luer Lock or Slip hub 52, which is held in position by the friction fitting (i.e. interference fit) provided by the tapered male connector tip 10 and the internal thread 26 on the collar 24 engaging with the hub 52. FIG. 3a also shows more detail of the locking member 30. Here it can be seen more clearly that the locking member 30 extends from the base portion 4. The locking member 30 is connected to the base portion 4 by a living hinge 54 which allows the locking member 30 to pivot forwards when acted upon by a user. The locking member 30 further comprises a first locking surface 56 and a second locking surface 58. The structure of the locking member 30 is such that it extends through the aperture 28 on the lever member 6 allowing it to be easily accessed by a user.

In the first position seen in FIG. 3a, the lever member 6 is in a locked position, whereby the underside 60 of the lever member 6 rests against the locking surface 56. In this position the lever member 6 cannot be pivoted and so the flexible hose cannot be clamped, nor can the hub 52 be removed using the lever member 6.

FIG. 3b shows a rear view of the fluid transfer connector 2 in the locked configuration seen in FIG. 3a. In this configuration the hose 50 is not clamped and therefore allows fluid to freely flow through. It can be seen in FIG. 3b that the cross section of the hose 50 is largely circular and will allow fluid to flow therethrough. The hose 50 may rest in contact with the hose clamp 12 but has not yet been deformed by active engagement.

FIG. 3c shows the fluid transfer connector 2 after the locking member 30 has been pushed forwards to release the lever member 6. When the locking member 30 has been pushed forwards, for example by a user's thumb when operating the fluid transfer connector 2, the first locking surface 56 moves forwards and away from the underside 60 of the lever member 6, unlocking the lever member 6 and allowing it to be pivoted. It can be seen in FIG. 3c that the lever member 6 has been pivoted downwards to a second position. Once pivoted downwards by a sufficient amount the clamping member 34 comes into contact with the hose 50. As the lever member 6 is pressed upon by a user, the clamping member 34 acts to deform the hose 50 thereby acting to clamp the hose 50 in the second position.

Additionally, as the lever member 6 is depressed, the front surface 18 moves towards the base of the hub 52, and the internal thread 26 moves away from the hub 52. Due to the spacing between the front surface 18 of the lever member 6 and the base of the hub 52 in the locked position (seen in FIG. 3a), as the lever member 6 is initially pivoted, and the clamping member 34 clamps down on the hose 50, the hub 52 is not acted upon by the front surface 18 until the lever has been pivoted through a certain angle. This arrangement of a spacing between the hub 52 and the front surface 18 ensures that the hose 50 is clamped before the hub 52 becomes disconnected thereby preventing or reducing the amount of fluid which may leak from the fluid transfer connector 2 during clamping and disconnection.

FIG. 3d shows a rear view of the fluid transfer connector 2 in the configuration seen in FIG. 3c. The hose 50 is now engaged in the hose clamp 12. Here it can be seen that the clamping member 34 clamps down onto the hose 50, which is at least partially forced into the V-shaped opening 14 and into the elongate slot 16 which runs along the base portion 4. In this second position the flexible hose 50 is clamped such that fluid can no longer flow through the hose 50. In this example, the clamping member 34 acts to press the hose 50 against the side surfaces of the slot 16 so as to deform the flexible hose 50 and interrupt the fluid flow through the hose 50.

FIG. 3e shows the fluid transfer connector 2 when the lever member 6 has been fully depressed to a third position. As the lever member 6 is fully depressed the clamping member 6 forces the hose 50 fully into the elongate slot 16 (not seen), thereby permanently clamping the hose 50. As the lever member 6 is pivoted further through its range of motion, the collar 24 comprising the internal thread 26 is moved away from the hub 52 thereby releasing the screw thread connection and additionally the front surface 18 acts on the base of the hub 52. As the lever member 6 is pressed the front surface 18 pushes the hub 52 along the male connector tip 10 to release the interference fitting, thereby releasing the hub 52 from the fluid transfer connector 2.

At this stage, the lever member 6 is latched in the third position. This latch is achieved by a top surface 62 of the lever member 6 being engaged by the second locking surface 58 on the locking member 30. Accordingly, at this stage, the hose 50 is fully clamped, the hub 52 has been released from the male connector tip 10 and the lever member 6 is latched in a third position in which the clamping member 34 is in contact with the hose 50 thereby holding it in the clamped position.

It will be appreciated that the hose may be made from a flexible (e.g. plastics) material such that when clamped in the elongate slot 16 it remains there in a clamped position without the need for any member to hold it in place. However, it will be appreciated that if the hose 50 is made from a material with sufficient resiliency, the hose 50 may tend to try to return to its natural shape and therefore may try to move out of the elongate slot 16. The arrangement shown in FIG. 3e, where the lever member 6 is locked in the clamping position, prevents the hose 50 from being removed.

Figure 3F:
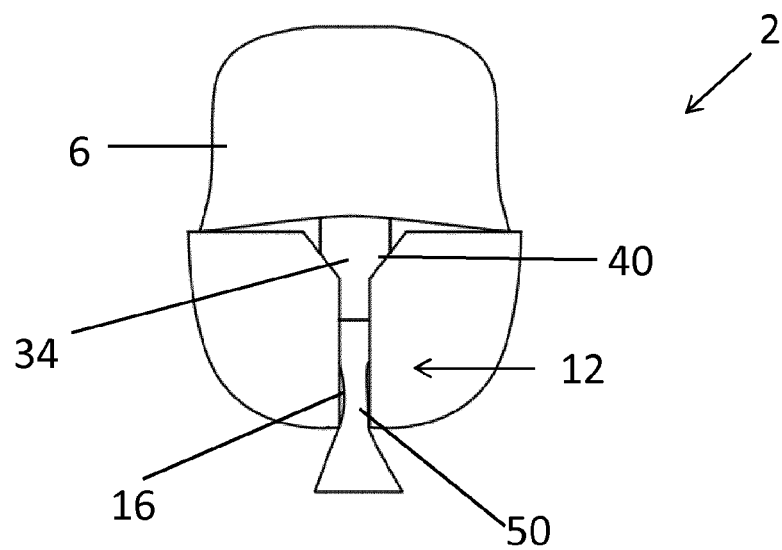

FIG. 3f shows a rear view of the fluid transfer connector 2 in the configuration seen in FIG. 3e. Here it can be seen that the lever member 6 has been pivoted to the point at which the clamp member 34 has forced the hose 50 through the V-shaped opening 14 and fully into the elongate slot 16 of the hose clamp 12.

Figure 4:
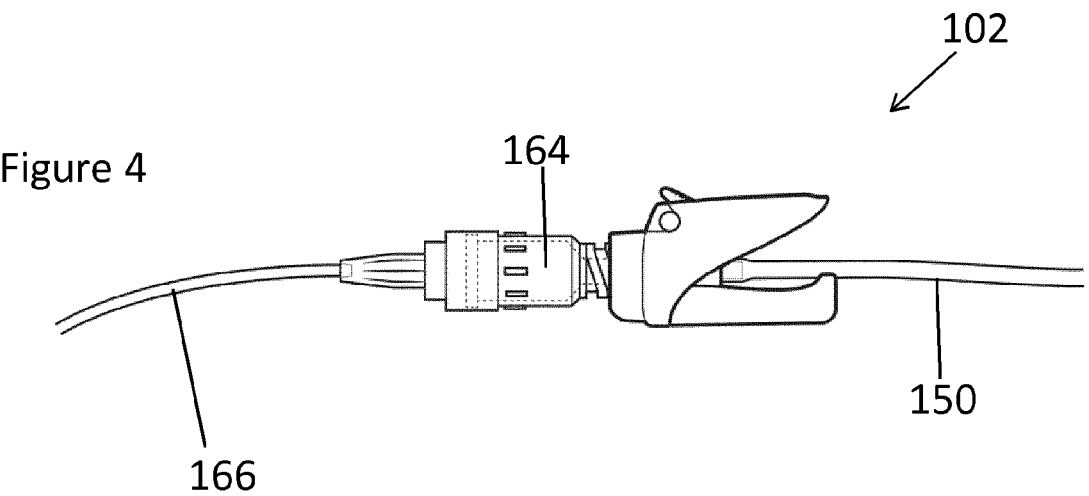
FIG. 4 shows a second embodiment of a fluid transfer connector connected to fluid lines.

FIG. 4 shows a fluid transfer connector 102 with an attached hose 150 connected to a female Luer Lock hub 164. The Luer Lock hub 164 is attached to the end of a second hose 166. The fluid transfer connector 102 effective provides an interface between the hose 150 and the Luer Lock hub 164.

Figure 5A:
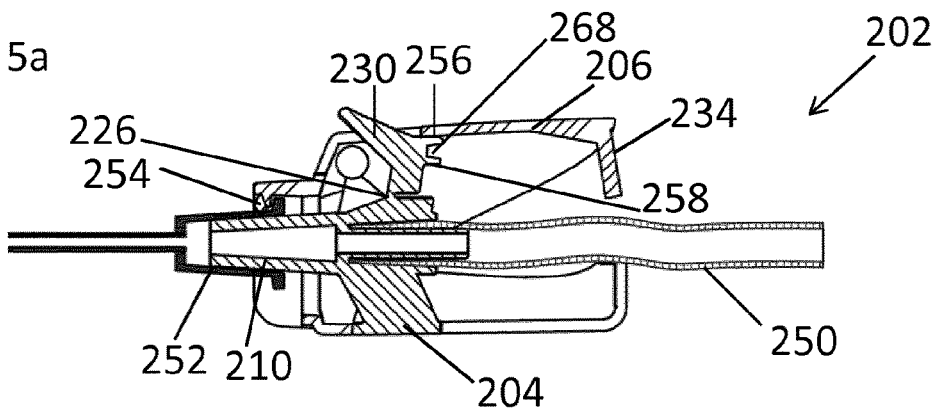
FIGS. 5a-f shows operational steps of a third embodiment of a fluid transfer connector which comprises a three-position locking member

FIGS. 5a-f show a further embodiment of a fluid transfer connector 202. The fluid transfer connector 202 essentially comprises the same features as the fluid transfer connector 2 seen in earlier Figures, except the fluid transfer connector 202 comprises a different locking member 230. FIG. 5a shows the fluid transfer connector 202 in which the locking member 230 can be seen. As with the earlier embodiment, the locking member 230 extends from the base portion 204 and is connected via a living hinge 254. Also, similarly to the earlier embodiment, the locking member 230 comprises a first locking surface 256 and second locking surface 258. In this embodiment, however, the locking member 230 further comprises an intermediate locking recess 268. The intermediate locking recess is located between the first locking surface 256 and second locking surface 258.

FIG. 5a shows the lever member 206 in the locked first position wherein the underside 260 of the lever member 206 rests against the first locking surface 256 on the locking member 230. In this first position, the hub 252 is held on the male connector tip 210 by the internal thread 226 and the interference fit with the male connector tip 210. The clamp member 234 is held away from the hose 250 and fluid is free to flow.

Figure 5B:
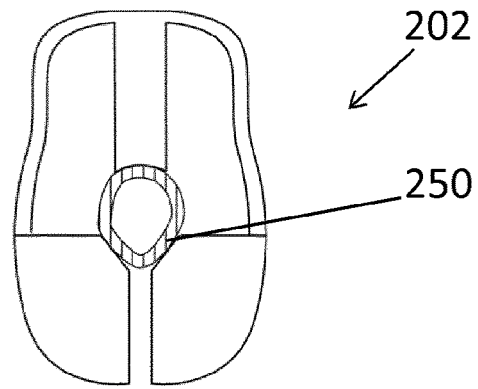

FIG. 5b shows a view from the rear of the fluid transfer connector 202 in the configuration seen in FIG. 5b. In this configuration the cross section of the hose 250 is its natural cross section and is open to allow fluid to pass through.

Figure 5C:
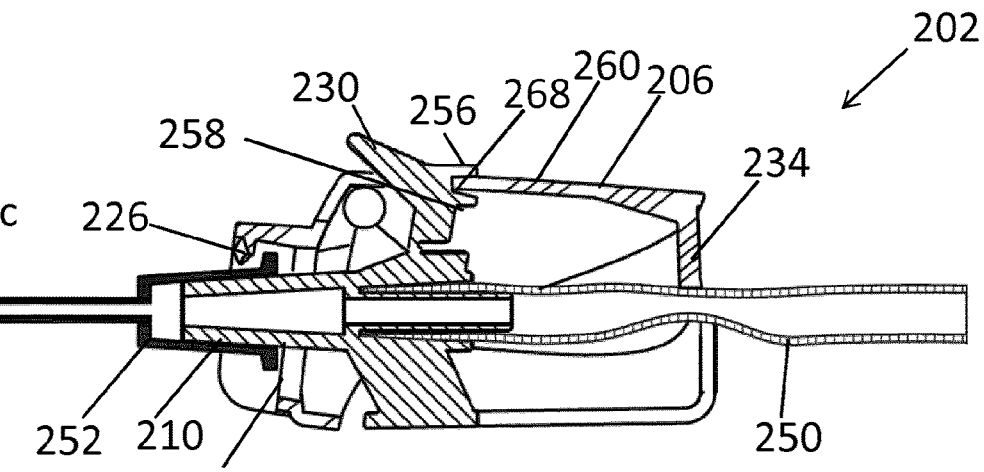

FIG. 5c shows the fluid transfer connector 202, after a user has pushed the locking member 230 forward to disengage the first locking surface 256 and the underside 260 of the lever member 260, allowing pivotal movement of the lever member 206 to the second position. It can be seen in FIG. 5c that as the lever member 206 is pivoted, before the lever member 206 is locked in position by the second locking surface 258, it comes into engagement with the intermediate locking recess 268. The intermediate locking recess 268 is arranged on the locking member 230 in a position such that when the lever member 206 is engaged, and locked in position, by the intermediate locking recess 268, the clamp member 234 is acting on the hose 250 to deform and clamp it to interrupt the flow of fluid. Further, in this intermediate second position, the front surface 218 has been moved towards the hub 252 and the screw thread 226 has begun to be moved away from the hub, however, importantly, the hub 52 has not yet been released from the male connector tip 210.

The advantage of locking member 230 comprising an intermediate locking recess 268 is that the fluid transfer connector 202 can be used to interrupt or stop the flow through the connector without necessarily disengaging the hub 252. This is advantageous in certain situations, for example when a user wants to temporarily stop the flow, but does not necessarily want to remove the hub 252. This effectively allows the fluid transfer connector 202 to acts as an ON/OFF valve.

Figure 5D:
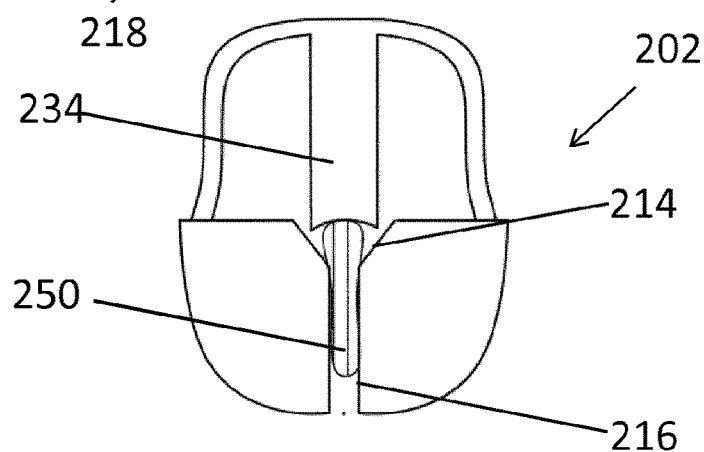

FIG. 5d shows a rear view of the fluid transfer connector 202 in the second position seen in FIG. 5c. In this position the clamp member 234 has pushed the hose 250 into the V-shaped opening 214 and partially into the elongate slot 216. The cross section of the hose 250 has been deformed such that fluid can no longer flow through it.

Figure 5E:
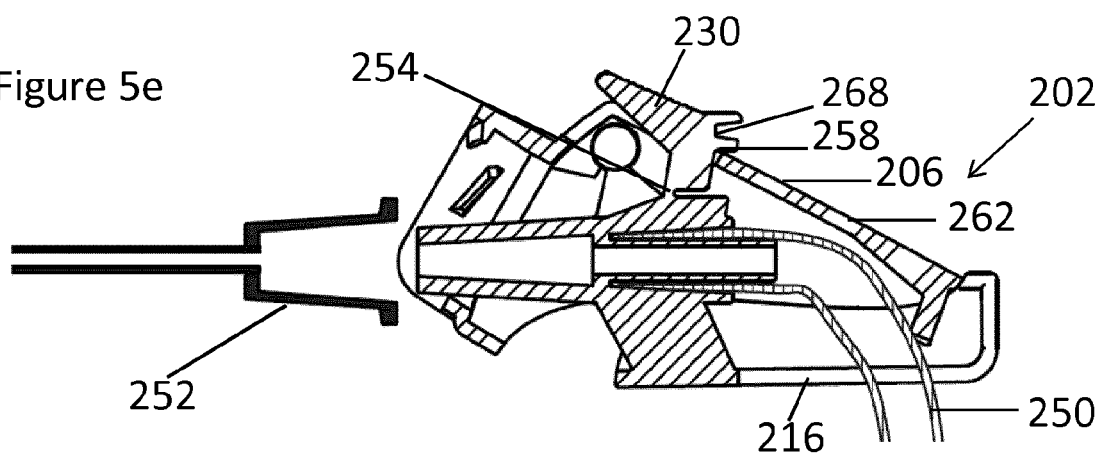

FIG. 5e shows the fluid transfer connector 202 when the lever member 206 has been fully depressed, thereby clamping the hose 250 fully into the elongate slot 216 and disconnecting the hub 252. Prior to this third position, in order to move the lever member 206 out of the intermediate locked position, a user must first push the locking member 230 forwards thereby pivoting it about its living hinge 254. Once the locking member 230 has been pivoted forwards, releasing the intermediate locking recess 268 the lever member 206 can then be pivoted downwards into the third position seen in FIG. 5e. Once in this position, the lever member 206 is again latched in position by engagement of the second locking surface 258 and the top surface 262 of the lever member 206.

Figure 5F:
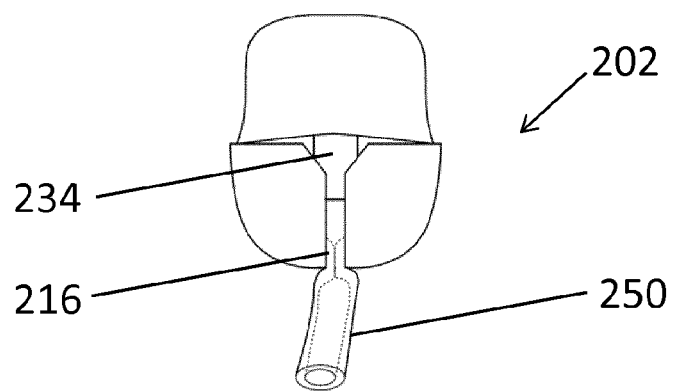

FIG. 5f shows a rear view of the fluid transfer connector 202 and illustrates how, in the third position seen in FIG. 5e, the clamp member 234 has pushed the hose 250 fully into the elongate slot 216. The cross section of the hose 250 within the slot 216 is deformed such that fluid cannot pass through the hose 250.

Figure 6:
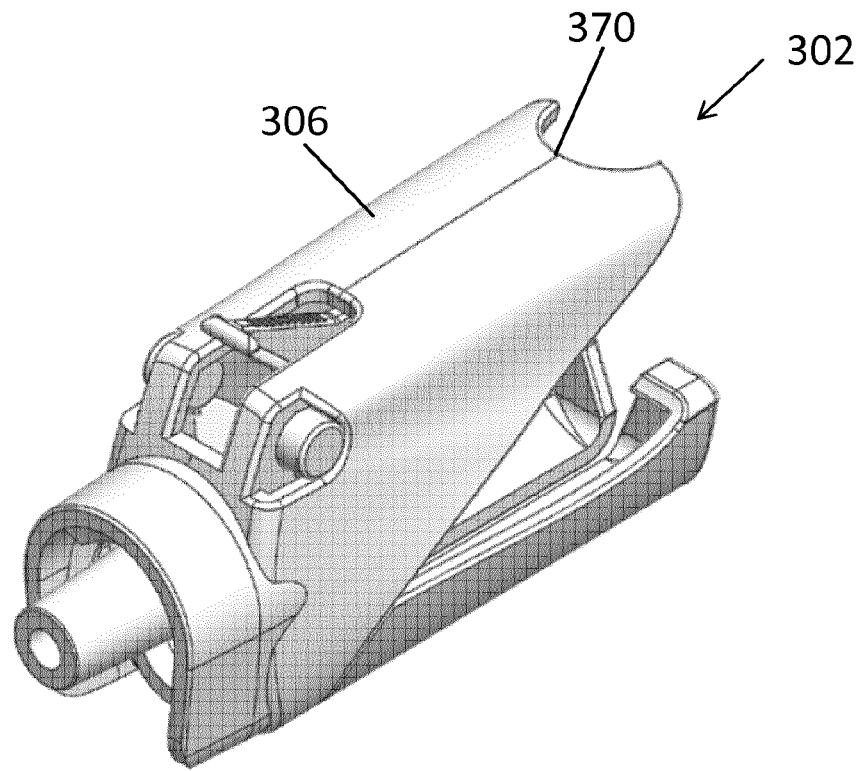
FIG. 6 shows a perspective view of a fourth embodiment of a fluid transfer connector.
Figure 7:
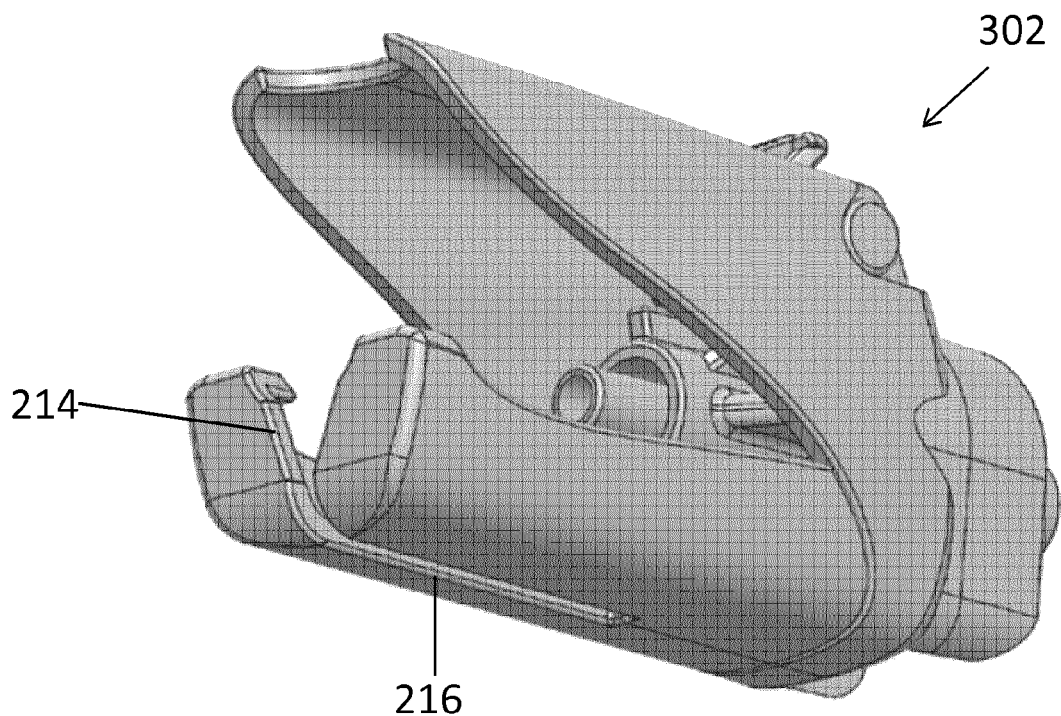
FIG. 7 shows a rear perspective view of the fluid transfer connector seen in FIG. 6

FIGS. 6 and 7 show perspective views of an alternative embodiment of a fluid transfer connector 302. As seen in FIG. 6, the fluid transfer connector 302 comprises many of the same features as the fluid transfer connector 2 seen in FIG. 1. The main difference is the lever member 306 which comprises a hemi-circular cut-out 270 at the rear of the lever member 306. The purpose of the cut-out 270 will be explained below with respect to FIGS. 8a-f.

FIG. 7 shows a perspective view from the rear of the fluid transfer connector 302. Unlike the embodiment seen in FIG. 1, the lever member 306 does not comprise a clamp member. Instead, in this embodiment, clamping of a hose (not shown) is achieved by a user manually pulling the hose into the V-shaped section 314 and into the elongate slot 316, as will be described below.

Figure 8A:
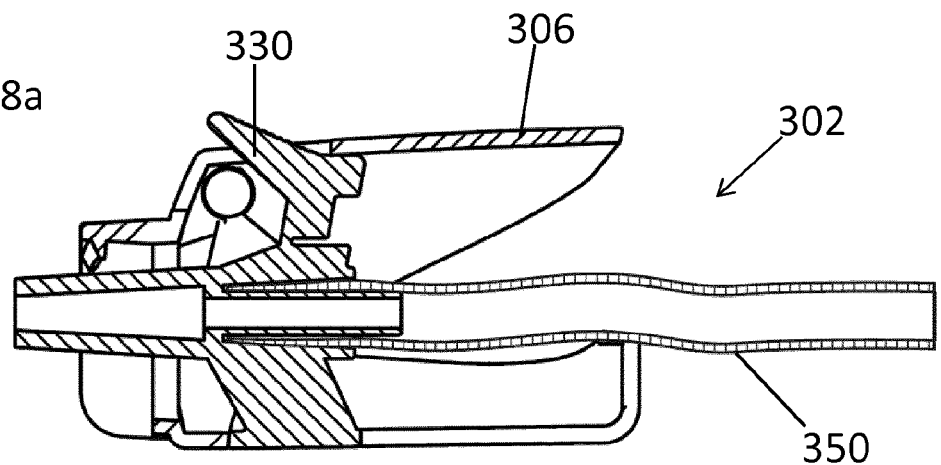
Figure 8B:
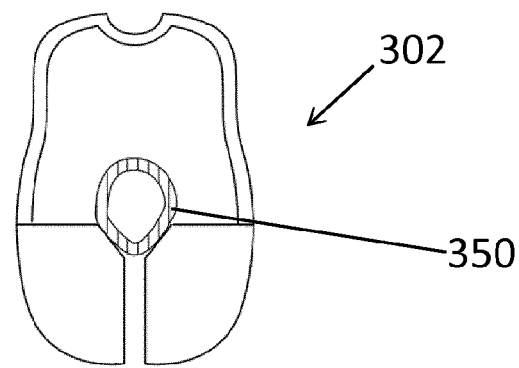

FIG. 8a shows the fluid transfer connector 302 connected to a hose 350 and a hub (not shown). In the position seen in FIG. 8a, the lever member 306 is held in a first position by the locking member 330 in the same manner as described above with reference to the fluid transfer connector 2. FIG. 8b shows a rear view of the fluid transfer connector 302, in the position seen in FIG. 8a, and illustrates how the cross section of the hose 350 is unchanged and therefore allows fluid to pass through.

FIG. 8c shows the fluid transfer connector 302 in the configuration in which the lever member 306 has been pivoted downwards. The locking member 330 functions in the same manner as described above with respect to the first embodiment, and in the configuration seen in FIG. 8c it can be seen that the lever member 306 is locked in its pivoted position. Due to the cut-out 370, which can be seen more clearly in FIG. 8d, when the lever member 306 is fully pivoted downwards, it does not deform the hose 350 as the cut-out 370 receives the hose 350. Preferably, the cut-out 370 has a profile which is matched to the profile of the hose 350. FIG. 8d shows a rear view of the fluid transfer connector 302 and more clearly illustrates how the cut-out 370 receives the hose 350 and does not act to deform it. In the position shown in FIGS. 8c and 8d, whilst not shown any hub attached to the male connector tip 310 will have been disconnected.

As the hose 350 is not clamped by operation of the lever member 306 a user must clamp the hose 350 by separate operation. This can be seen in FIGS. 8e and 8f. As user must pull the hose 350 into the V-shaped opening 314 and then into the elongate slot 316. This process may be carried out once the lever member 306 has been pivoted into the position seen in FIG. 8e, and any hub has been disconnected from the male connector tip 310, however, a user may clamp the hose 350 when a hub is still attached, i.e. when the lever member 306 has not been pivoted. This may be considered to be equivalent to the configuration described above with reference to FIG. 5a-f in which the hose 250 is clamped with the lever member 206 in an intermediate position.

Figure 9A:
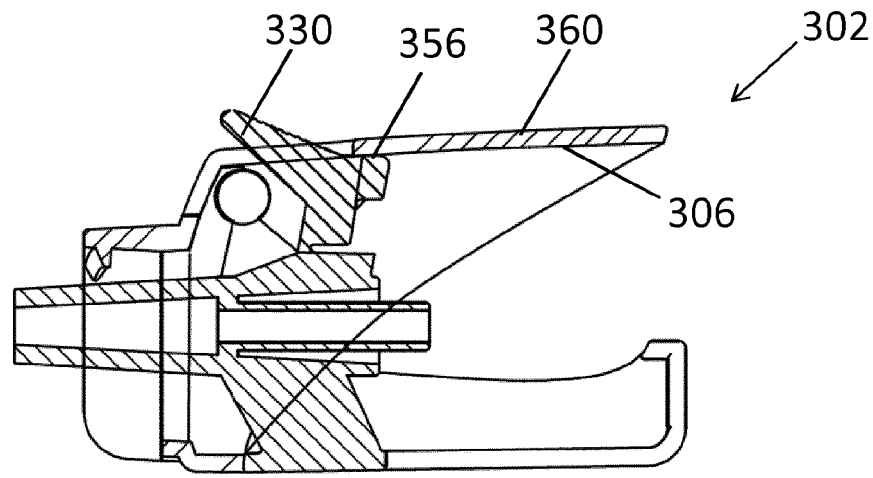
FIGS. 9a-d show operational steps for the locking member of the fluid transfer connector seen in FIG. 6 and FIG. 7.
Figure 9B:
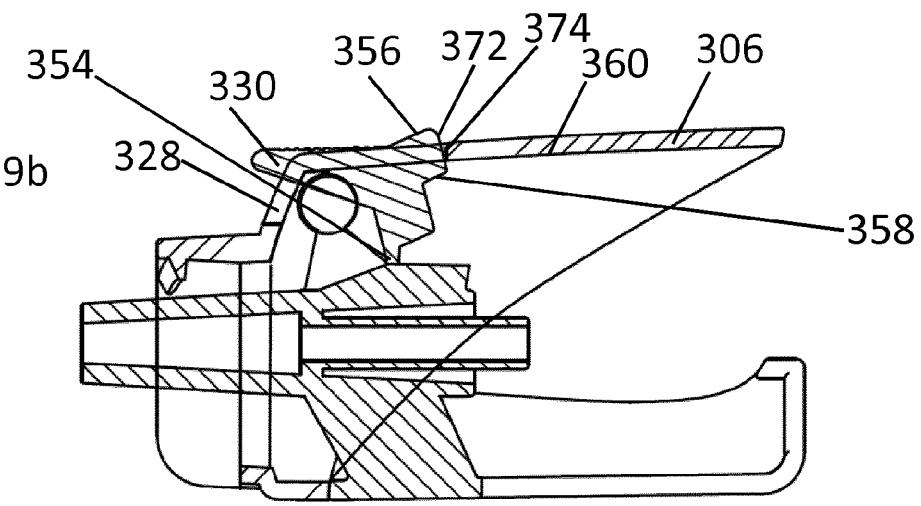

FIGS. 9a-9d show in more detail the release and locking of the locking member 330. Whilst operation of the locking member 330 is discussed in relation to the fluid transfer connector 302, it equally applies to any other embodiments encompassing a locking member with a similar profile and with an appropriate corresponding lever member. FIG. 9a shows the lever member 306 in the locked first position. As discussed previously, the lever member 306 is held in the locked position by the first locking surface 356 engaging with the underside 360 of the lever member 306. This engagement prevents the lever member 306 from being pivoted downwards.

Figure 9C:
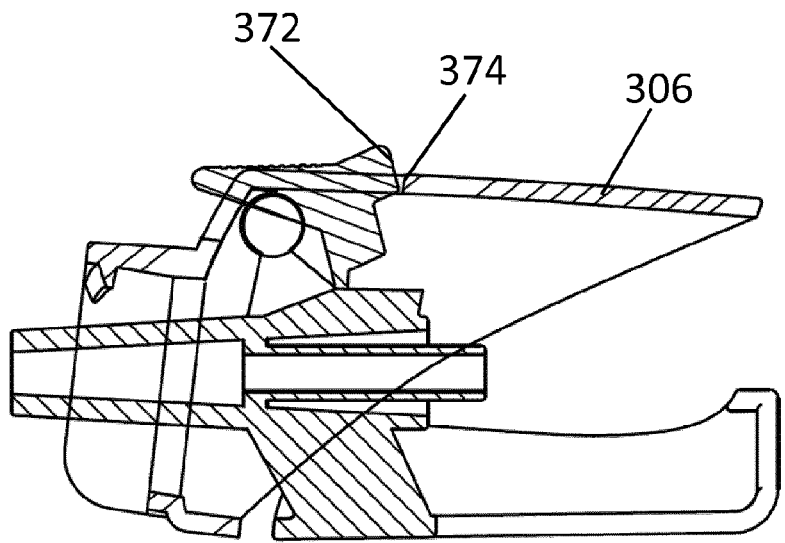
Figure 9D:
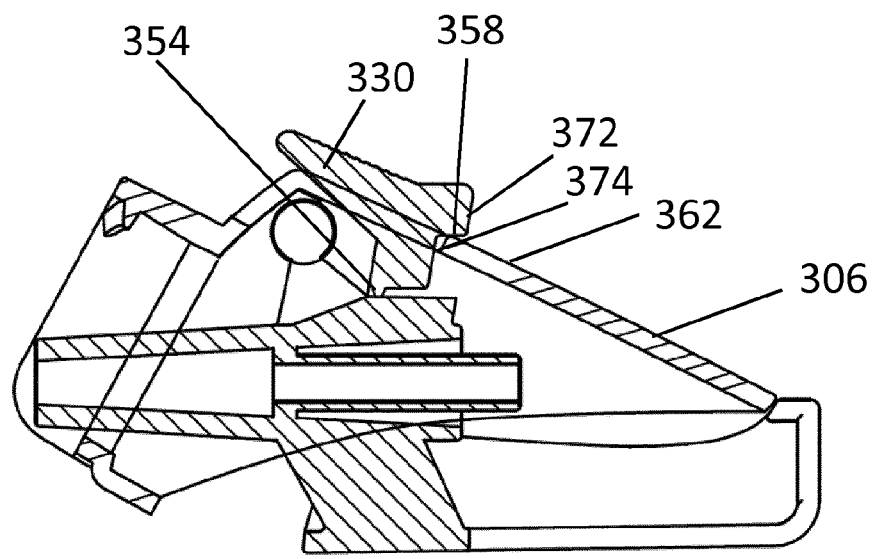

When a user wants to operate the lever member 306, they must first release the engagement of the first locking surface 356 and the underside 360 of the lever member 306. This can be achieved, for example, by a user pushing the locking member 330 forwards with their thumb, this will cause the lever member 330 to pivot about the living hinge 354. Once the engagement between the first locking surface 356 and the underside 360 of the lever member 306 has been released, the lever member 306 can be pivoted downwards. This can be seen in FIG. 9b. Typically, as the lever member 306 is pivoted downwards a user will release the locking member 330. A rear surface 372, of the locking member, which links the first locking surface 356 and the second locking surface 358 moves into contact with edge portion 374 of the of the aperture 328 on the lever member 306. This aperture 328 is the same as the aperture 28 as seen in FIG. 1. Due to the contact between the rear surface 372 and the edge portion 374 the locking member 330 is prevented from moving backwards and locking the lever member 306. FIG. 9c shows further progression of the lever member 306 through its pivotal motion. As the lever member 306 is pivoted further, the edge portion 374 moves towards the bottom of the rear surface 372.

As the lever member 306 is pivoted further, the edge portion 374 moves past the end of the rear surface 372, at which point the locking member 330 pivots backwards due to the resiliency provided by the living hinge 354. The result of the pivotal motion of the locking member 330 is that the lever member 306 once again is latched in position as the locking member 330 pivots backwards and the second locking surface 358 engages with the top surface 362 of the lever member 306. This latched position can be seen in FIG. 9d.

If a user wishes to release the lever member 306, and allow it to pivot back upwards, they must first push the locking member 330 forwards to release the engagement between the second locking surface 358 and the top surface 362 of the lever member 306.

Figure 10:
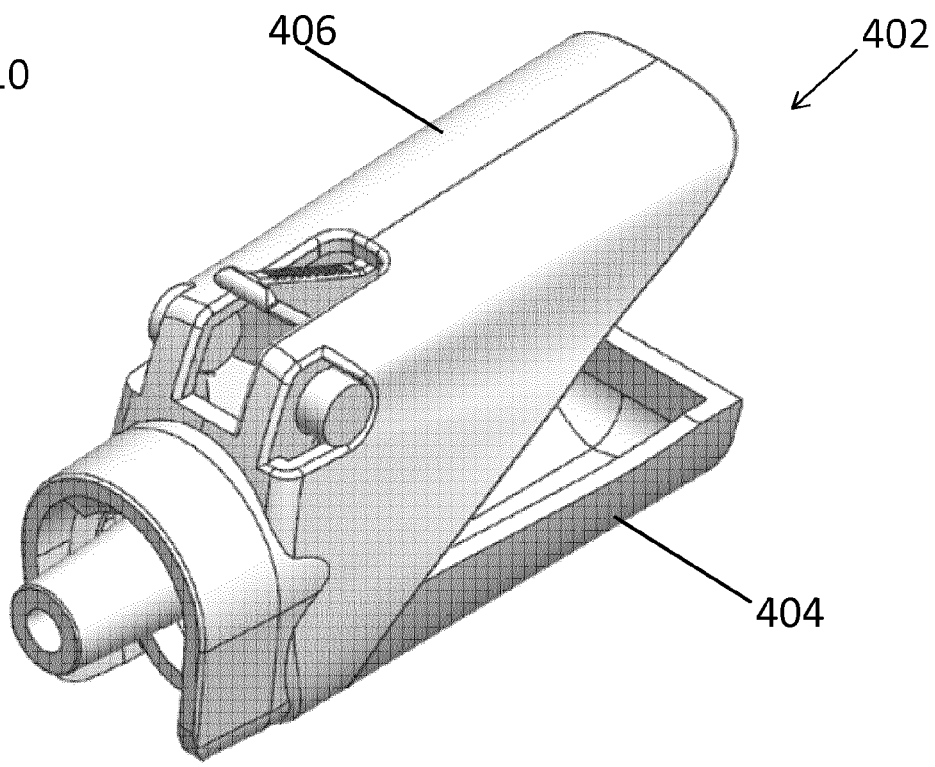
FIG. 10 shows a perspective view of a fifth embodiment of a fluid transfer connector.
Figure 11:
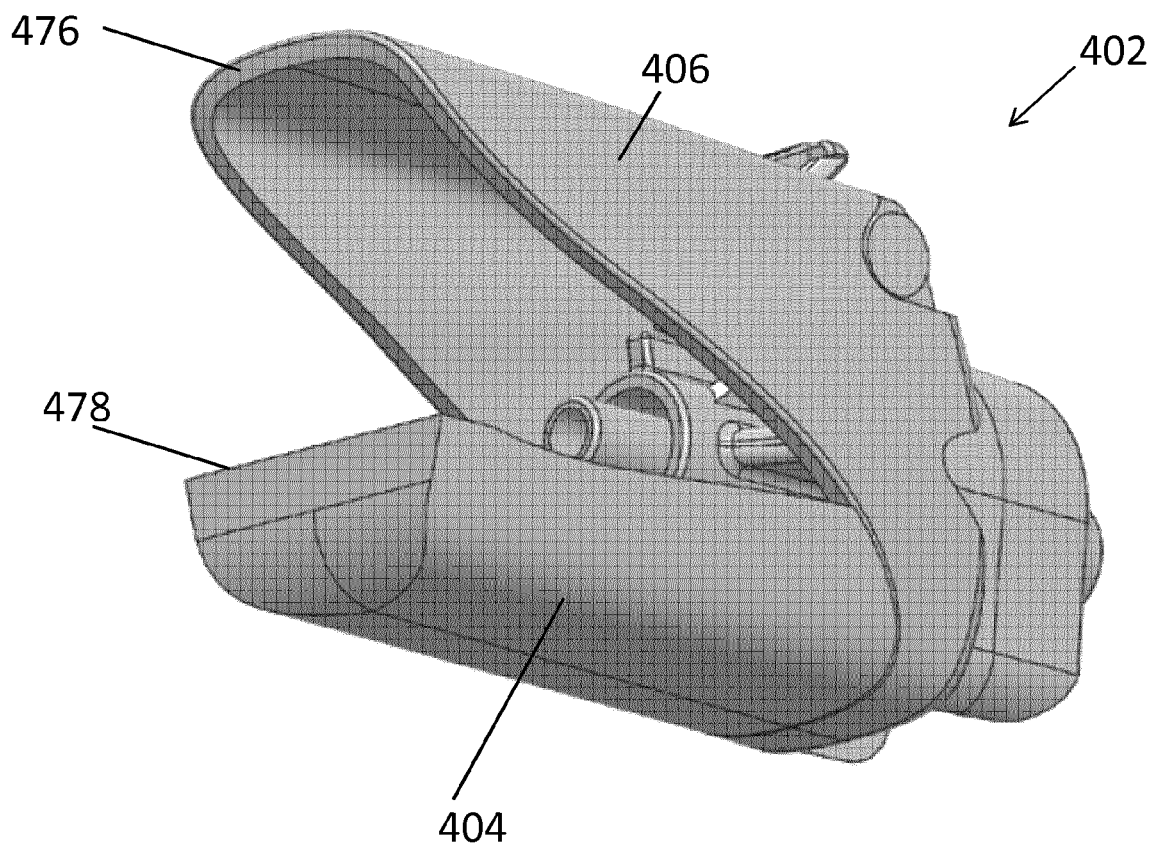
FIG. 11 shows a rear perspective view of the fluid transfer connector seen in FIG. 10.

FIGS. 10 and 11 show perspective views of further embodiments of a fluid transfer connector 402 in accordance with an embodiment of the present invention. As seen in FIG. 10, the fluid transfer connector 402 shares many features with earlier embodiments, however, it differs in that it does not comprise a clamping arrangement in the base portion 404, additionally the lever member 406 does not comprise any clamp member or cut-away portion.

FIG. 11 shows a rear perspective view of the fluid transfer connector 402. Here it can be seen more clearly that the lever member 406 does not comprise a discernible clamping member. Instead, in this embodiment, as will become more apparent later in discussion of FIGS. 12a-b, clamping of a hose is achieved as the rear edge 476 of the lever member and the rear edge 478 are brought together as the lever member 406 is pivoted.

Figure 12A:
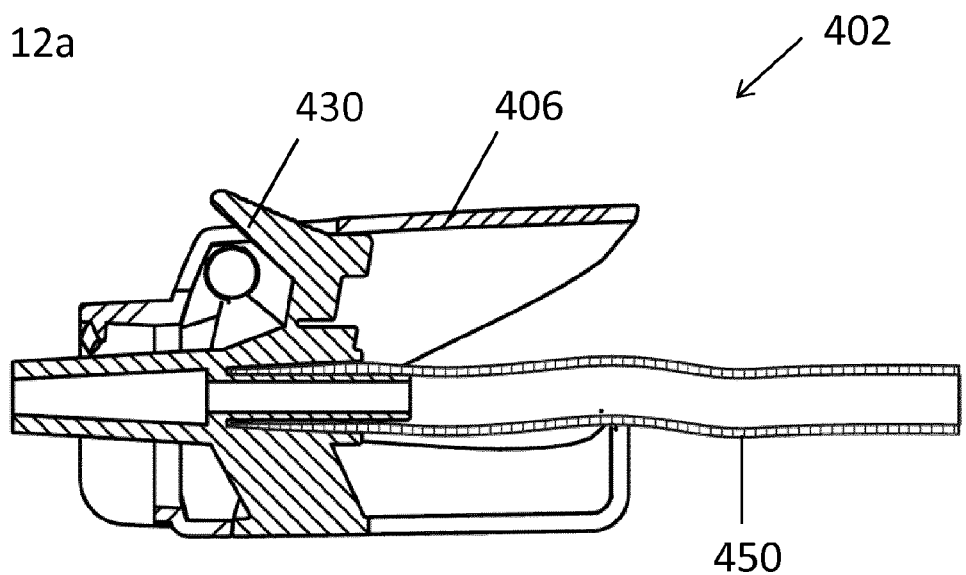
FIGS. 12a-b show operational steps of the fluid transfer connector seen in FIG. 10 and FIG. 11.
Figure 12B:
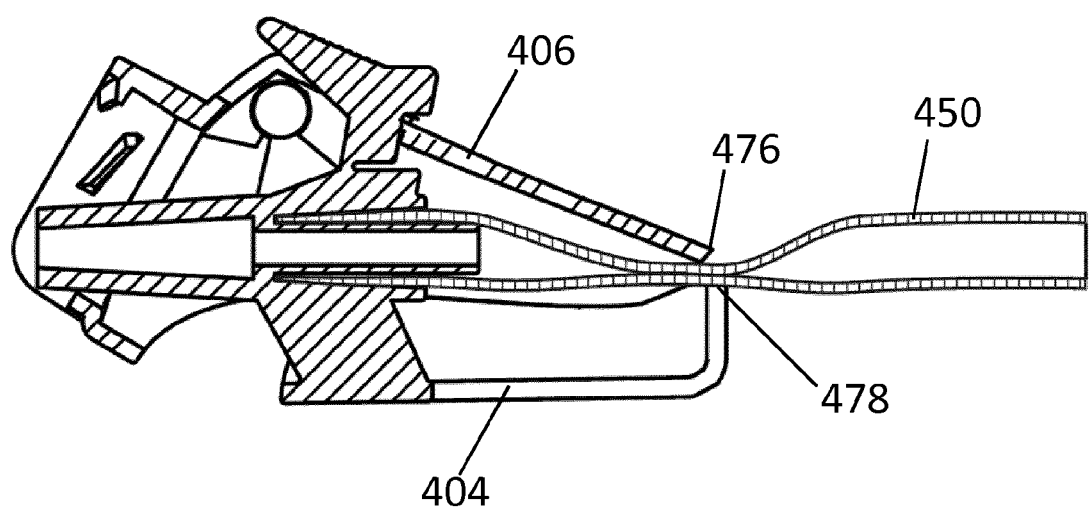

FIG. 12a shows the fluid transfer connector 402 with a hose 450 attached and a hub (not shown) also attached. In FIG. 12a the fluid transfer connector 402 is shown in the locked arrangement in which the locking member 430 locks the lever member 406 in position. This locking member 430 functions in an identical manner to the locking member discussed above, e.g. with respect to FIGS. 9a-d.

As with previous embodiments, when a user wishes to clamp the hose 450 and disconnect a hub, they must first unlock the lever member 406 by pivoting the locking member 430 forwards. Once this has occurred and the lever member 406 is free to pivot, a user may press down on the lever member 406. This can be seen I FIG. 12b, which shows the lever member 406 in the depressed position. In the depressed position the rear edge 476 of the lever member and the rear edge 478 of the base portion are brought together which results in the clamping of the hose 450 between these two edges. The hose 450 is deformed by this clamping motion which prevents the flow of fluid through the hose 450. One of the advantages of the fluid transfer connector 402 seen in FIGS. 10-12a-b, is that the fluid transfer connector is relatively simple and therefore may be easier to make than other embodiments.

However, unlike other embodiments, with the fluid transfer connector 402 it is not possible to leave the hose 450 clamped when the lever member 406 is pivoted back to its original position, i.e. in a position in which the screw threads on the collar engage with a hub on the male connector tip.

Figure 13A:
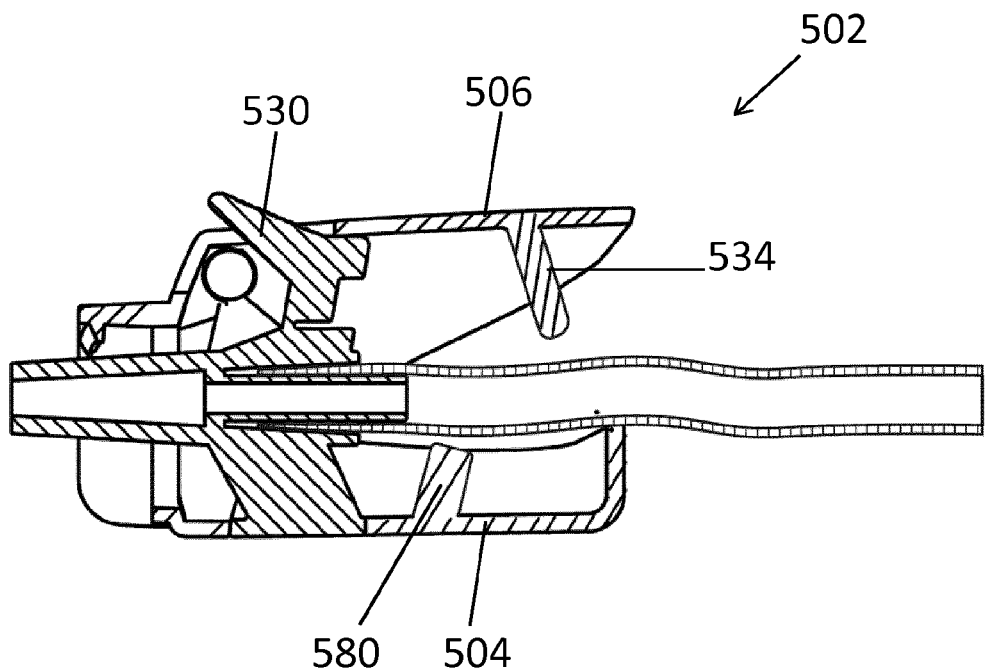
FIGS. 13a-b show cross sectional views of a sixth embodiment of a fluid transfer connector.
Figure 13B:
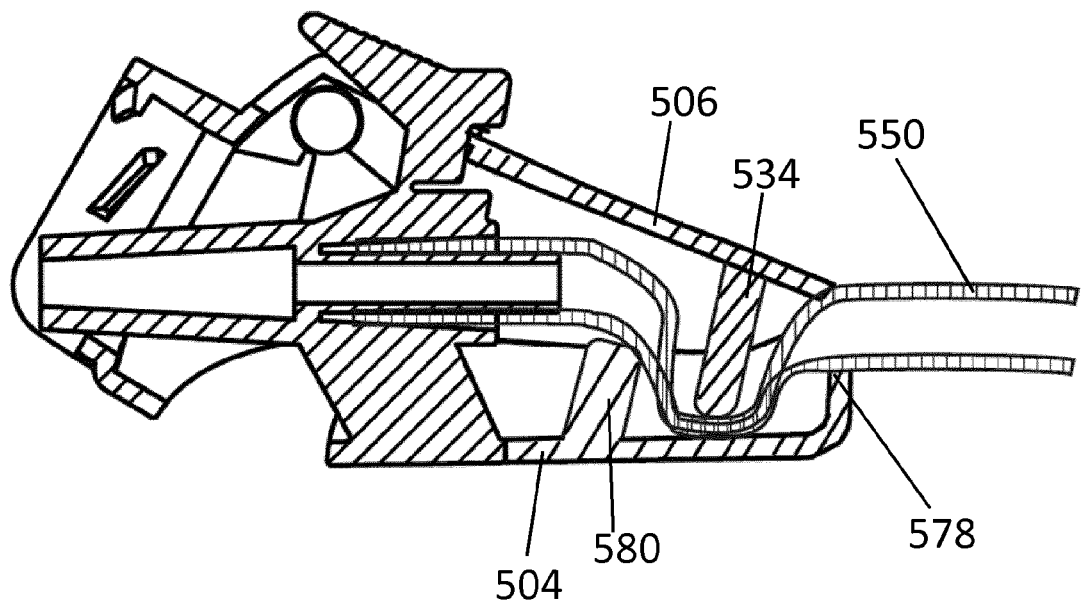

FIGS. 13a and 13b show a cross sectional side view of a further embodiment of a fluid transfer connector 502. Many of the features of the fluid transfer connector 502 are the same as previous embodiments, however, unlike in the first embodiment which comprises a clamping arrangement in the form of a clamping member extended from the rear end of the lever member, and a v-shaped opening and an elongate slot, the fluid transfer connector 502 instead comprises a clamp member 534 positioned partially along the length of the lever member 506. On the base portion 504 is a corresponding protrusion 580. The fluid transfer connector 502 is operated in a similar manner to earlier embodiments in which the lever member 306 is locked by the locking member 530 and which must be moved before the lever member 506 can be pivoted.

Clamping of the hose 550 can be seen in FIG. 13*b*. As the lever member 506 is pivoted downwards, the clamp member 534 is brought into contact with the hose 550. As the lever member 506 is pushed further, the clamp member 534 drives the hose 550 downwards causing the hose to bend and deform between the protrusion 580 and the rear edge 578 of the base portion 504. As the lever member 506 is fully depressed, the hose 550 immediately below the clamp member 534 is flattened thereby preventing any fluid from flowing through the hose 550.

Figure 14A:
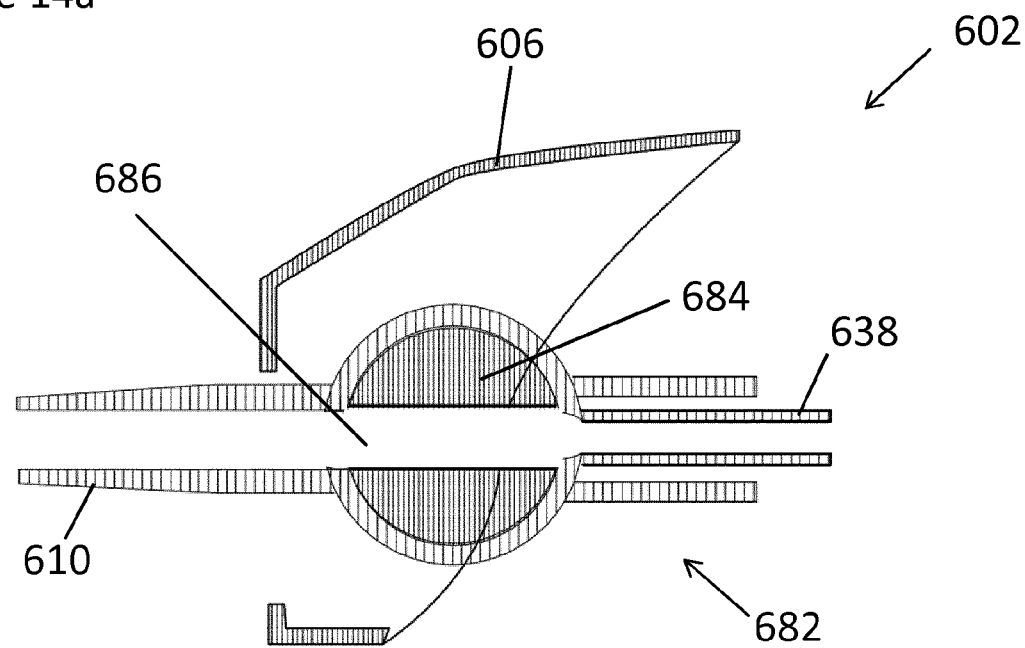
FIGS. 14a-b show schematic views of a seventh embodiment of a fluid transfer connector.
Figure 14B:
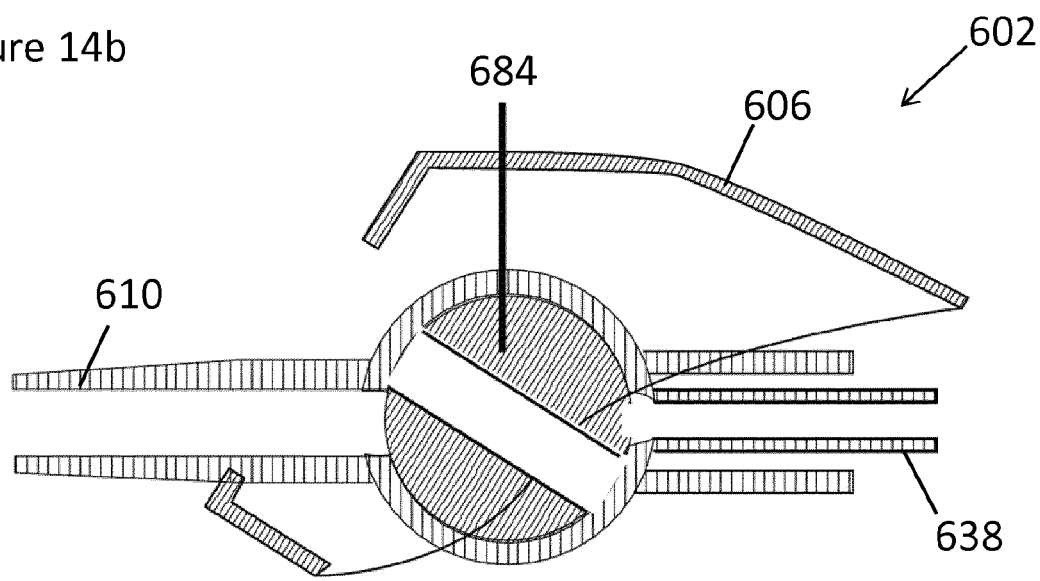

FIGS. 14*a* and 14*b* show an illustrative drawing of another fluid transfer connector 602 in accordance with an embodiment of the present invention. The fluid transfer connector 602 functions in a different way to previous embodiments which clamp a flexible tubing hose attached to the fluid transfer connector, instead the fluid transfer connector 602 prevents flow through by operating an internal valve 682. The valve 680 comprises a valve part or body 684 which defines a fluid channel 686 therethrough. The valve body 684 is operatively connected to the lever member 606 such that when the lever member 606 pivots, the valve body 684 rotates. FIG. 14*a* shows the fluid transfer connector 602 in the first position in which fluid can flow through the connector 602. In this position the valve part or body 684 is positioned such that the flow channel 686 is aligned with the male connector tip 610 and the internal male connector tip 638.

FIG. 14*b* shows the fluid transfer connector 602 when the lever member 606 has been pivoted to the second position and the fluid flow has been blocked. It can be seen that the pivotal movement of the lever member 606 rotates the valve part or body 684 within the valve 682 thereby moving the fluid channel 686 out of alignment with the male connector tip 610 and the internal male connector tip 638. In this position fluid can no longer flow through the connector 602. The valve body 684 and lever member 606 may be operatively connected by any suitable means.

Whilst not shown, the fluid transfer connector 602 seen in FIGS. 14*a* and 14*b* may comprise many of the features of the earlier embodiments, for example the locking member and the internally threaded collar which may extend from a front portion of the lever member 606. As with earlier embodiments, the lever member 606 may also function to disconnect a hub from the male connector tip 610 if desired. Such a connector 602 may optionally be connected to a flexible tubing hose, although it will be appreciated that interruption of the fluid flow does not rely on deforming a flexible hose as in the previous embodiments.

Figure 15A:
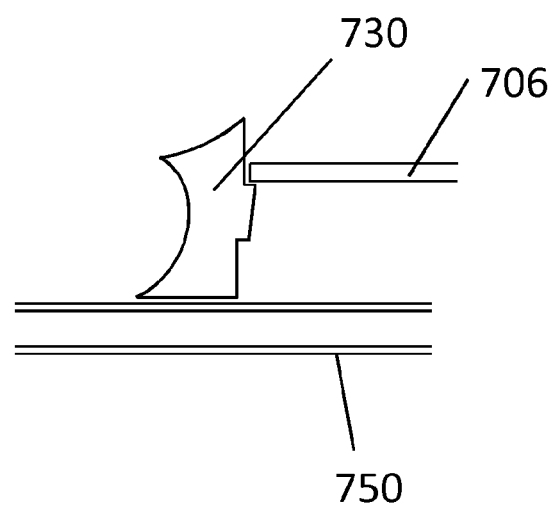
FIGS. 15a-15b show schematic views of a clamping mechanism of an eighth embodiment of fluid transfer connector.
Figure 15B:
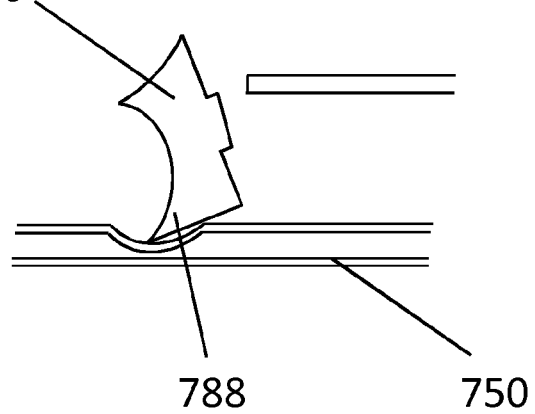

FIGS. 15*a* and 15*b* illustrate a further arrangement which can be used to interrupt the flow of fluid through a connector. In this embodiment, the locking member 730 provides a dual function of locking the lever member 706 and also functions to deform the flexible hose 750 to stop the flow of fluid through the connector. FIG. 15*a* shows the locking member 730 functioning to lock the lever member 706 and prevent any pivotal motion.

When a user wishes to operate the lever member 706, e.g. to disconnect a hub from the connector, they must first operate the locking member 730. This can be seen in FIG. 15*b*, when the locking member 730 is pivoted forwards, the base 788 of the locking member 730 presses into the hose 750 thereby deforming it and preventing fluid flow through the hose 750. Whilst in the example shown the locking member 730 acts on a hose 750 which is attached to the connector, the locking member 730 may act on an integral part of the connector, e.g. the connector may comprise an integral hose proximal to the locking member 730 which can be deformed by the locking member 730.

Figure 16:
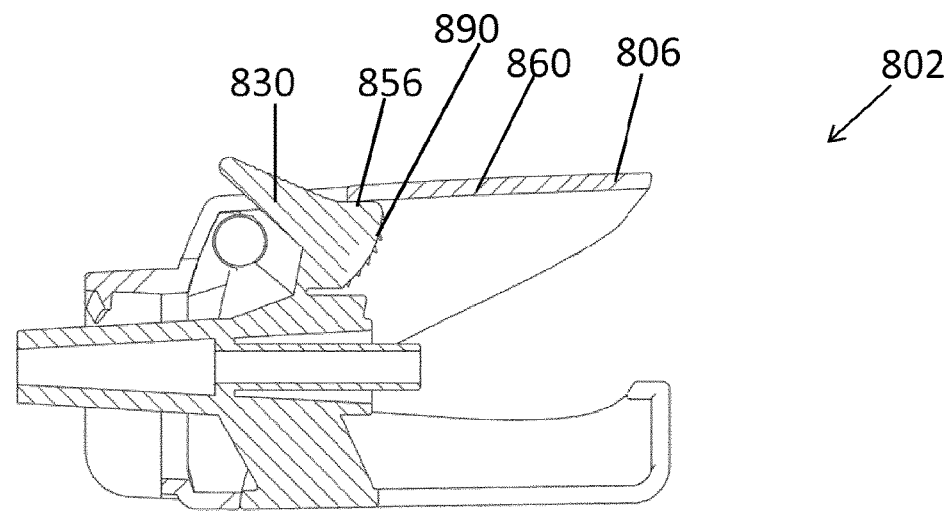
FIG. 16 shows a cross sectional view of a ninth embodiment of a fluid transfer connector.

FIG. 16 shows another fluid transfer connector 802 in accordance with an embodiment of the present invention. The fluid transfer connector 802 shares many of the same features as the embodiments seen in earlier Figures, the main difference being that the locking member 830 comprises a plurality of ratchet teeth 890. As with embodiments discussed above, the lever member 806 is locked in a first position by the first locking surface 856 engaging with the underside 860 of the lever member 806. Once the locking member 830 has been pivoted forwards, thereby releasing the lever member 806, the lever member 806 may be pivoted downwards. The ratchet teeth 890 located on the rear of the locking member 830 enable the lever member 806 to be locked in a series of positions. Accordingly, with this embodiment, in addition to fully clamping the hose, it may be possible to partially clamp a hose and thereby partially reduce the flow rate through the connector 802 as opposed to completely stopping the flow rate. This embodiment may therefore be used to control the flow rate through the connector 802. Additionally, the ratchet teeth 890 may allow the connector 802 to be used with hoses of different diameters, where otherwise it would not be possible to lock the lever member 806.

Figure 17A:
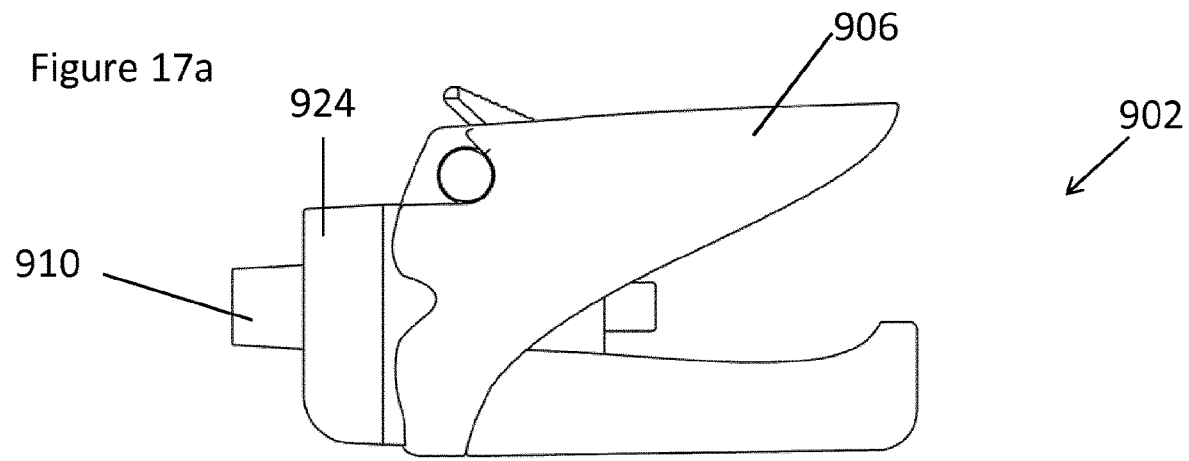
FIGS. 17a-b show side views of a tenth embodiment of a fluid transfer connector.
Figure 17B:
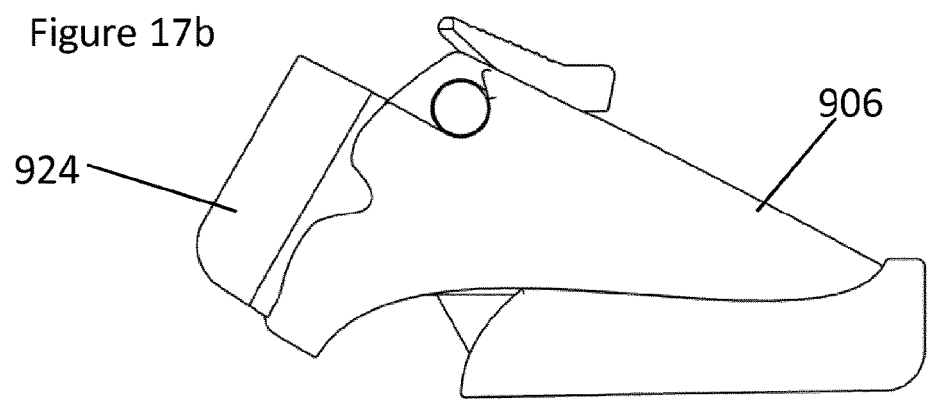

As will be appreciated, contamination and sterility of medical equipment is a major concern. Fluid transfer connectors within a medical environment may be used multiple times and so there is a risk between uses of parts of the connector becoming contaminated, of particular concern is the connector tip, which provides the means for engaging the connector with another component. If this part becomes contaminated, then it may cause contamination of fluid passing through the connector. FIG. 17*a* shows a side view of a fluid transfer connector 902 having a lever member 906 carrying a hemi-circular collar 924 at its forward end which partially surrounds and extends along the male connector tip 910 in a similar manner to many of the embodiments discussed above. The hemi-circular collar 924 extends significantly downwards beyond the male connector tip 910 such that when the lever member 906 is pivoted the hemi-circular collar 924 moves to surround the male connector tip 910. This can be seen in FIG. 17*b*. Here the male connector tip 910 is now shielded by the hemi-circular collar 924. Whilst the hemi-circular collar 924 may not completely surround the male connector tip 910, by moving forwards closer to the end of the male connector tip 910 it will largely prevent the male connector tip 910 from coming into contact with other objects and therefore help to reduce the risk of contamination.

Figure 18:
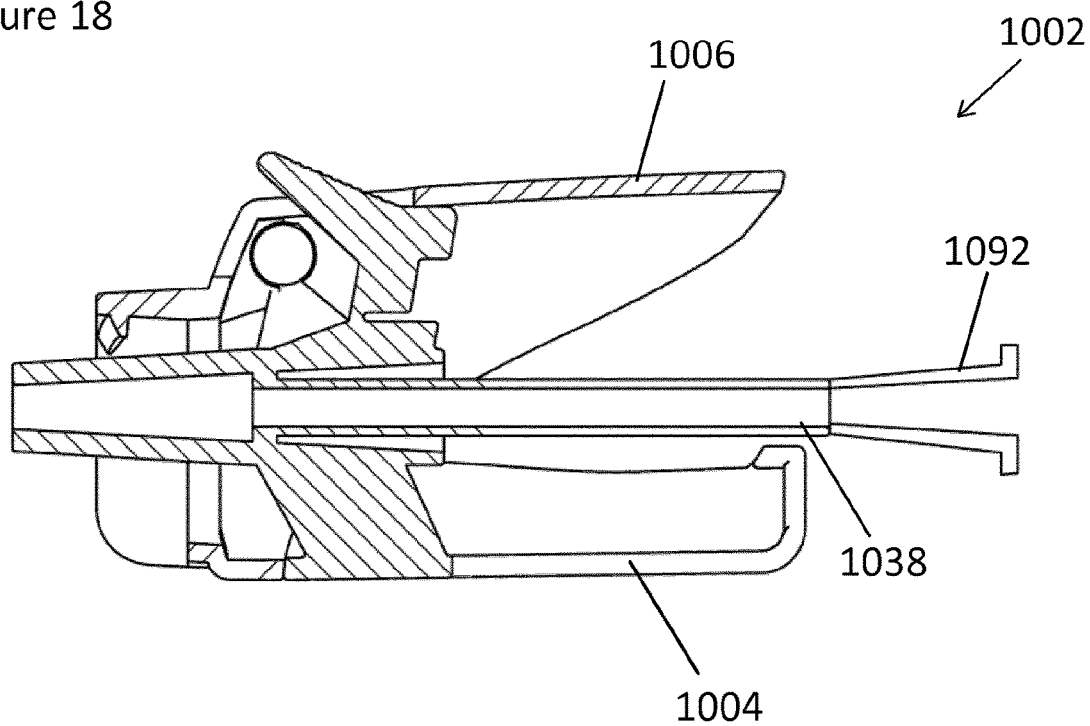
FIG. 18 shows a cross sectional view of an eleventh embodiment of a fluid transfer connector.

In the embodiments discussed above, many of the fluid transfer connectors comprise an internal male connector tip for connecting to a hose. In the embodiments shown the internal male connector tip is shown to be contained within the connector largely surrounded by the lever member and base portion. FIG. 18 shows an alternative embodiment of a fluid transfer connector 1002 in which the internal connector part 1038 extends out of the rear of the fluid transfer connector 1038 and forms a female Luer connector part 1092. Extending out and away from the lever member 1006 and base portion 1004 may make it easier for a user to connect to the female Luer connector part 1092. The female Luer connector part 1092 also facilitates the connection of a male tip to the fluid transfer connector 1002. This extended internal connector part 1038 may be added to any of the embodiments discussed above or below.

Figure 19:
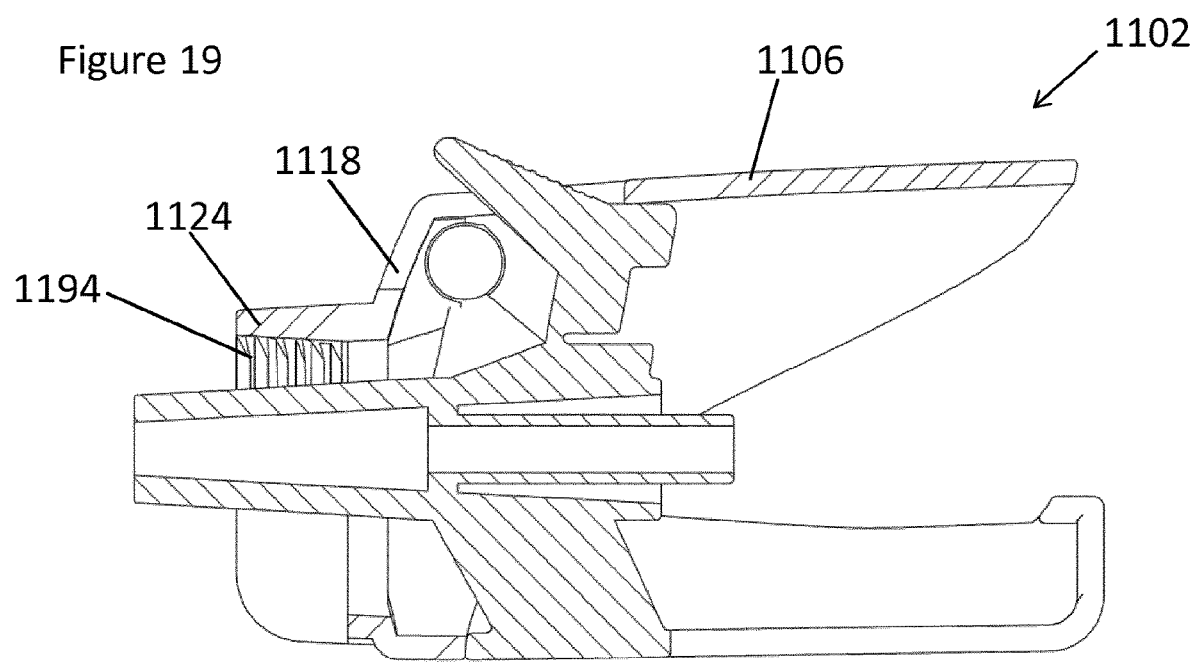
FIG. 19 shows a cross sectional view of a tenth embodiment of a fluid transfer connector.

FIG. 19 shows another fluid transfer connector 1102 according to another embodiment of the invention. In this embodiment, instead of a screw thread within a collar extending from the forward portion of the lever member, this embodiment comprises a lever member 1106 having a hemi-circular collar 1124 extending from a front surface 1118 which comprises a series of ratchet teeth 1194. Accordingly, the fluid transfer connector 1102 may be connected to hubs which comprise a rim, as opposed to hubs which comprise an external screw thread which are better suited to collars comprising an internal screw thread.

In the embodiments discussed comprising a locking member, the locking member is provided as a pivotally mounted member which pivots about an axis, which may be provided by a living hinge. However, the Applicant has recognised that the locking member may be slidably mounted.

In many of the embodiments discussed above, the lever member may be resiliently biased such that once depressed and subsequently released by a user, the lever member will return to its original first position. The resilient bias may be provided by a separate resilient member, e.g. a spring, which acts on the lever member. Alternatively, a resilient bias may be provided by the lever member itself. For example, the lever member may be made from a resilient deformable material and the lever member may be mounted such that as the lever member is depressed, it is caused to deform which provides a resilient bias which tends to move the lever member back to its original position. This may be achieved, for example, by providing protrusions on the base portion of the fluid transfer connector, about which the lever member deforms as it is pivoted.

In any of the embodiments described above, a hose may be removably attached to the fluid transfer connector by any suitable means, e.g. a Luer Slip fitting or a Luer Lock fitting. Alternatively, a hose may be permanently attached to the fluid transfer connector, e.g. via welding or any other suitable means.

In the various embodiments described above, there is seen a Luer connector part in the form of a tapered male connector tip which defines a fluid transfer port therethrough. However, it will be appreciated that any of the fluid transfer connectors in these embodiments may instead comprise another, i.e. non-Luer, medical standard connector part comprising a fluid transfer port. The medical standard connector part may be any connector part meeting the requirements of one of the ISO 80369 series of small-bore connector standards. For example, instead of a Luer connector part, the medical standard connector part may be an ENFit connector part or an NRFit connector part.

The invention claimed is:

1. A fluid transfer connector, the connector comprising:
a medical standard connector part comprising a fluid transfer port;
a fluid transfer channel in fluid communication with the fluid transfer port; and
a moveable member, wherein the moveable member is arranged to:
interrupt the fluid communication between the fluid transfer channel and the fluid transfer port when the moveable member is moved from a first position to a second position; and
release a connection, in use, between the medical standard connector part and a corresponding adaptor part by pushing against the corresponding adaptor part when the moveable member is moved (i) from the first position to the second position and/or (ii) from the second position to a third position;
wherein the moveable member is further arranged to block or cover the fluid transfer port when the moveable member is moved from the first position to the second position or to a further position.

2. A fluid transfer connector according to claim 1, wherein the moveable member is arranged to release the connection when the moveable member is moved from the second position to a third position.

3. A fluid transfer connector according to claim 1, wherein the moveable member is arranged to interrupt the fluid communication by moving a valve part to at least partially block the fluid communication with the fluid transfer port in the second position.

4. A fluid transfer connector according to claim 1, further comprising a locking member to hold the moveable member in the first position.

5. A fluid transfer connector according to claim 1, wherein the moveable member comprises a lever member pivotally mounted to the fluid transfer connector.

6. A fluid transfer connector according to claim 1, wherein the moveable member comprises a threaded collar.

7. A fluid transfer connector according to claim 1, wherein the connection between the medical standard connector part and the corresponding adaptor part comprises at least a friction fitting.

8. A fluid transfer connector according to claim 1, wherein the medical standard connector part comprises a connector part meeting the requirements of one of the ISO 80369 series of small-bore connector standards.

9. A fluid transfer connector according to claim 8, wherein the medical standard connector part comprises an ENFit connector part, an NRFit connector part, or a Luer connector part.

10. A fluid transfer connector comprising:
a Luer connector part comprising a fluid transfer port having a tapered surface to form a friction fitting with a corresponding Luer part;
a fluid transfer channel in fluid communication with the fluid transfer port;
a moveable member, wherein the moveable member is arranged to:
interrupt the fluid communication between the fluid transfer channel and the fluid transfer port when the moveable member is moved from a first position to a second position; and
release the friction fitting with the corresponding Luer part when the moveable member is moved (i) from the first position to the second position and/or (ii) from the second position to a third position, wherein the moveable member is arranged to move along the tapered surface of the Luer connector part to push away the corresponding Luer part.

11. A fluid transfer connector according to claim 10, wherein the moveable member is arranged to release the friction fitting when the moveable member is moved from the second position to a third position.

12. A fluid transfer connector according to claim 10, wherein the moveable member is arranged to interrupt the fluid communication by moving a valve part to at least partially block the fluid communication with the fluid transfer port in the second position.

13. A fluid transfer connector according to claim 10, further comprising a locking member to hold the moveable member in the first position.

14. A fluid transfer connector according to claim 10, wherein the moveable member comprises a lever member pivotally mounted to the fluid transfer connector.

15. A fluid transfer connector according to claim 10, wherein the moveable member comprises a Luer Lock engagement part.

16. A fluid transfer connector comprising:
- a medical standard connector part comprising a fluid transfer port;
- a fluid transfer channel in fluid communication with the fluid transfer port; and
- a moveable member comprising a threaded collar, wherein the moveable member is arranged to:
  - interrupt the fluid communication between the fluid transfer channel and the fluid transfer port when the moveable member is moved from a first position to a second position; and
  - release a connection, in use, between the medical standard connector part and a corresponding adaptor part by pushing against the corresponding adaptor part when the moveable member is moved (i) from the first position to the second position and/or (ii) from the second position to a third position.

* * * * *